(12) United States Patent
Abe et al.

(10) Patent No.: US 11,214,652 B2
(45) Date of Patent: *Jan. 4, 2022

(54) ORGANIC GROUP-MODIFIED ORGANOSILICON RESIN, PRODUCTION METHOD THEREOF, AND COSMETIC

(71) Applicant: SHIN-ETSU CHEMICAL CO., LTD., Tokyo (JP)

(72) Inventors: Takuya Abe, Annaka (JP); Masayuki Konishi, Tokyo (JP); Chihiro Hayakawa, Tokyo (JP); Masanao Kamei, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/768,147

(22) PCT Filed: Nov. 29, 2018

(86) PCT No.: PCT/JP2018/043991
§ 371 (c)(1),
(2) Date: May 29, 2020

(87) PCT Pub. No.: WO2019/107497
PCT Pub. Date: Jun. 6, 2019

(65) Prior Publication Data
US 2020/0332065 A1    Oct. 22, 2020

(30) Foreign Application Priority Data

Nov. 30, 2017 (JP) .............................. JP2017-230494

(51) Int. Cl.
*A61K 8/89* (2006.01)
*A61Q 17/04* (2006.01)
*A61Q 1/00* (2006.01)
*C08G 77/14* (2006.01)

(52) U.S. Cl.
CPC ............. *C08G 77/14* (2013.01); *A61K 8/89* (2013.01); *A61Q 1/00* (2013.01); *A61Q 17/04* (2013.01)

(58) Field of Classification Search
CPC . C08G 77/14; A61K 8/89; A61Q 1/00; A61Q 17/04
See application file for complete search history.

(56) References Cited

U.S. PATENT DOCUMENTS

| | | | |
|---|---|---|---|
| 5,422,412 | A | 6/1995 | Morita et al. |
| 5,684,112 | A | 11/1997 | Berthiaume et al. |
| 5,958,448 | A | 9/1999 | Ekeland et al. |
| 10,626,222 | B2 * | 4/2020 | Abe |

FOREIGN PATENT DOCUMENTS

| | | |
|---|---|---|
| JP | 2-25411 A | 1/1990 |
| JP | 4-45155 A | 2/1992 |
| JP | 7-53718 A | 2/1995 |
| JP | 7-196449 A | 8/1995 |
| JP | 8-239475 A | 9/1996 |
| JP | 8-319351 A | 12/1996 |

OTHER PUBLICATIONS

International Search Report (PCT/ISA/210) issued in PCT/JP2018/043991 dated Mar. 5, 2019.
Written Opinion (PCT/ISA/237) issued in PCT/JP2018/043991 dated Mar. 5, 2019.

* cited by examiner

*Primary Examiner* — Alma Pipic
(74) *Attorney, Agent, or Firm* — Birch, Stewart, Kolasch & Birch, LLP

(57) ABSTRACT

This organic group-modified organosilicon resin is represented by the average composition formula (1).

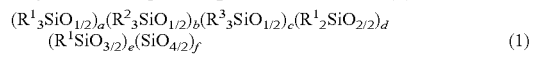

$$(R^1{}_3SiO_{1/2})_a(R^2{}_3SiO_{1/2})_b(R^3{}_3SiO_{1/2})_c(R^1{}_2SiO_{2/2})_d (R^1SiO_{3/2})_e(SiO_{4/2})_f \quad (1)$$

[a, b, c, d, e and f are numbers that satisfy $0 \leq a \leq 400$, $0 < b \leq 200$, $0 \leq c \leq 400$, $0 \leq d \leq 320$, $0 \leq e \leq 320$, $0 < f \leq 1{,}000$, and $0.5 \leq (a+b+c)/f \leq 1.5$.]

Because this organic group-modified organosilicon resin can form films softer than those formed with trimethylene siloxysilicate, the cosmetic obtained by blending with said silicon resin feels good when used, has good cosmetic holding properties, spreads easily and has an excellent finish, easy removal, and superior scratch resistance.

15 Claims, No Drawings

ORGANIC GROUP-MODIFIED ORGANOSILICON RESIN, PRODUCTION METHOD THEREOF, AND COSMETIC

TECHNICAL FIELD

The present invention relates to a novel organic group-modified organosilicon resin and to a cosmetic preparation containing the same.

BACKGROUND ART

The practice of including film-forming polymers in cosmetic preparations has hitherto been widely carried out for such purposes as to enhance the long-lasting performance of the cosmetic. In makeup cosmetics and sunscreen cosmetics in particular, the development of products having excellent water resistance, oil resistance (sebum resistance) and perspiration resistance is desired. Substances such as trimethylsiloxysilicic acid and silicone-modified acrylic polymers are used to this end.

However, when a hard film such as trimethylsiloxysilicic acid is included in a sufficient amount within a cosmetic material, the cosmetic following application has a poor feel to the touch, leading to a rough, unpleasant sensation. Another problem is that, because the film is brittle, when stress is applied, cracks arise in the film and sufficient oil resistance cannot be obtained. In order to compensate for these drawbacks, compositions have been disclosed in which highly polymerized dimethylpolysiloxanes are used together with the silicone resin (Patent Document 1: JP-A H04-45155). However, these film-forming agents give rise to stickiness on account of the highly polymerized dimethylpolysiloxane, and sufficient oil resistance is not obtained.

On the other hand, silicone-modified acrylic polymers form soft, highly adhesive films, and are able to impart desirable properties such as a smooth touch and lustrous feel to cosmetic preparations in which they are included (Patent Document 2: JP-A H02-25411). However, the film formed using such a silicone-modified acrylic polymer is of inadequate strength. Compositions which use such a silicone resin and a silicone-modified acrylic polymer together have been described (Patent Document 3: JP-A H07-196449). However, a sufficient oil resistance cannot be obtained with such compositions, and so they have not been effective for improving the long-lasting performance of cosmetics.

PRIOR ART DOCUMENTS

Patent Documents

Patent Document 1: JP-A H04-45155
Patent Document 2: JP-A H02-25411
Patent Document 3: JP-A H07-196449

SUMMARY OF INVENTION

Technical Problem

In light of the above circumstances, an object of this invention is to provide an organic group-modified organosilicon resin which has modifying groups such as polyether groups and silicone groups and which preferably is solid at room temperature. Additional objects are to provide a method for preparing such organic group-modified organosilicon resins, and cosmetic preparations containing such organic group-modified organosilicon resins.

Solution to Problem

The inventors have conducted extensive investigations in order to achieve these objects. As a result, they have discovered that, in an organic group-modified organosilicon resin of average compositional formula (1) below, by limiting the amount of modifying groups, the organosilicon resin prior to modification forms a strong film that is brittle, whereas, in the organic group-modified organosilicon resin following modification, such brittleness is ameliorated and a film that is softer than a trimethylsiloxysilicic acid film can be obtained, in addition to which the resistance to oils such as sebum is greatly enhanced compared with prior to modification. The inventors have also found that by including this organic group-modified organosilicon resin as a film-forming agent in a cosmetic material, there is no stickiness during application, the feeling on use is good, the water and oil resistances are both excellent and adhesion to the skin is good, thus enabling a cosmetic material to be obtained that is long-lasting, has a good spreadability and finish, is easy to remove and has an excellent rub-off resistance. These discoveries ultimately led to the present invention.

Accordingly, the present invention provides the following organic group-modified organosilicon resin, method of preparing the same, and cosmetic preparation containing the same.

1. An organic group-modified organosilicon resin having average compositional formula (1) below

[Chem. 1]

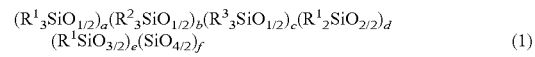

[wherein each $R^1$ is a like or unlike alkyl, aryl or aralkyl group of 1 to 30 carbon atoms, or a halogen-substituted group, amino-substituted group or carboxyl-substituted group thereof; each $R^2$ is a like or unlike polyoxyalkylene group of general formula (2) below

[Chem. 2]

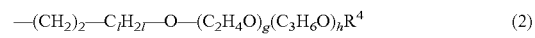

(wherein $R^4$ is a substituted or unsubstituted monovalent hydrocarbon group or a hydrogen atom, and the subscripts l, g and h are integers which satisfy the conditions $0 \leq l \leq 15$, $0 \leq g < 8$, $0 \leq h < 8$ and $0 < g+h < 8$), a polyglycerol group of general formula (3)

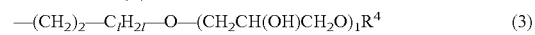

(wherein $R^4$ is a substituted or unsubstituted monovalent hydrocarbon group or a hydrogen atom, and the subscripts l and i are integers which satisfy the conditions $0 \leq l \leq 15$ and $0 < i \leq 5$) or $R^1$, with at least one $R^2$ being a polyoxyalkylene group of general formula (2) or a polyglycerol group of general formula (3); each $R^3$ is a like or unlike group of general formula (4), general formula (5), general formula (6) or general formula (7) below

[Chem. 3]

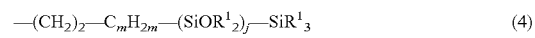

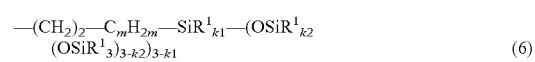

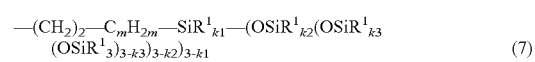

(wherein each $R^1$ is a like or unlike alkyl, aryl or aralkyl group of 1 to 30 carbon atoms, or a halogen-substituted group, amino-substituted group or carboxyl-substituted group thereof; and the subscripts m, j and k1 to k3 are integers which satisfy the conditions $0 \le m \le 5$, $0 \le j \le 500$, $0 \le k1 \le 2$, $0$ $k2 \le 2$ and $0 \le k3 \le 2$) or $R^1$, with at least one $R^3$ being a group of general formula (4), general formula (5), general formula (6) or general formula (7); and the subscripts a, b, c, d, e and f are numbers which satisfy the conditions $0 \le a \le 400$, $0 < b \le 200$, $0 \le c \le 400$, $0 \le d \le 320$, $0 \le e \le 320$, $0 < f \le 1{,}000$ and $0.5 \le (a+b+c)/f \le 1.5$].

2. The organic group-modified organosilicon resin of 1 above, wherein the subscripts b and c in average compositional formula (1) satisfy the conditions $0 < b \le 30$ and $0 \le c \le 30$;

if $R^2$ is a polyoxyalkylene group of general formula (2), subscripts g and h in general formula (2) are integers which satisfy the conditions $0 \le g \le 6$, $0 \le h \le 6$ and $0 < g+h \le 6$;

if $R^2$ is a polyglycerol group of general formula (3), the subscript i in general formula (3) is an integer which satisfies the condition $0 < i \le 3$; and if the subscript c satisfies the condition $0 < c \le 400$ and $R^3$ is a group of general formula (4), the subscript j in general formula (4) satisfies the condition $0 \le j \le 10$, which resin is a solid.

3. The organic group-modified organosilicon resin of 2 above, wherein the subscripts g and h in general formula (2) are integers which satisfy the conditions $0 \le g \le 5$, $0 \le h \le 5$ and $0 < g+h \le 5$, and the subscript i in general formula (3) is an integer which satisfies the condition $0 < i \le 2$.

4. The organic group-modified organosilicon resin of any of 1 to 3 above, wherein the weight-average molecular weight is from 1,000 to 100,000.

5. The organic group-modified organosilicon resin of any of 1 to 4 above which has a hydrophilic-lipophilic balance, as determined by Griffin's formula, of from 0.1 to 15.

6. A method for preparing the organic group-modified organosilicon resin of 1 above, which method includes the step of hydrosilylating a hydrosilyl group-containing organosilicon resin of average compositional formula (8) below

[Chem. 4]

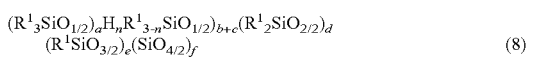

(wherein each $R^1$ is a like or unlike alkyl, aryl or aralkyl group of 1 to 30 carbon atoms, or a halogen-substituted group, amino-substituted group or carboxyl-substituted group thereof; the subscripts a, b, c, d, e, and f are integers which satisfy the conditions $0 \le a \le 400$, $0 < b \le 200$, $0 \le c \le 400$, $0 \le d \le 320$, $0 \le e \le 320$, $0 < f \le 1{,}000$ and $0.5 \le (a+b+c)/f \le 1.5$; and n is an integer that satisfies the condition $1 \le n \le 3$) with one or more compound that is selected from alkenyl group-terminated compounds of general formulas (9), (10), (11), (12), (13) and (14) below

[Chem. 5]

$$CH_2=CH-C_lH_{2l}-O-(C_2H_4O)_g(C_3H_6O)_hR^4 \quad (9)$$

$$CH_2=CH-C_lH_{2l}-O-(CH_2CH(OH)CH_2O)_iR^4 \quad (10)$$

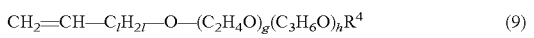

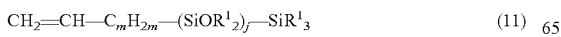

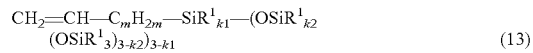

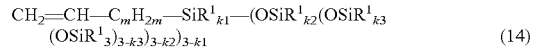

(wherein $R^4$ is a substituted or unsubstituted monovalent hydrocarbon group or a hydrogen atom, the subscripts l, g, h and i are integers which satisfy the conditions $0 \le l \le 15$, $0 \le g < 8$, $0 \le h < 8$, $0 < g+h < 8$ and $0 < i \le 5$; and the subscripts m, j and k1 to k3 are integers which satisfy the conditions $0 \le m \le 5$, $0 \le j \le 500$, $0 \le k1 \le 2$, $0 \le k2 \le 2$ and $0 \le k3 \le 2$) and includes a compound of general formula (9) or (10).

7. A cosmetic preparation which includes from 0.1 to 40 wt % of the organic group-modified organosilicon resin of any of 1 to 5 above.

8. The cosmetic preparation of 7 above which is a makeup cosmetic or a sunscreen cosmetic.

Advantageous Effects of Invention

Because the organic group-modified organosilicon resin of the invention has the ability to form a softer film than trimethylsiloxysilicic acid, cosmetic preparations formulated with this organosilicon resin have a good feel on use, are long-lasting, have a good spreadability and finish, are easy to remove and have an excellent rub-off resistance.

DESCRIPTION OF EMBODIMENTS

The invention is described in detail below.

The organic group-modified organosilicon resin of the invention has average compositional formula (1) below

[Chem. 6]

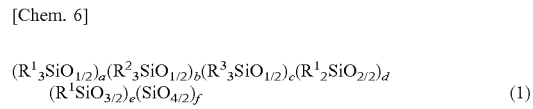

[wherein each $R^1$ is a like or unlike alkyl, aryl or aralkyl group of 1 to 30 carbon atoms, or a halogen-substituted group, amino-substituted group or carboxyl-substituted group thereof; each $R^2$ is a like or unlike polyoxyalkylene group of general formula (2) below

[Chem. 7]

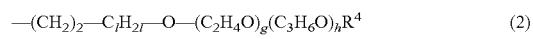

(wherein $R^4$ is a substituted or unsubstituted monovalent hydrocarbon group or a hydrogen atom, and the subscripts l, g and h are integers which satisfy the conditions $0 \le l \le 15$, $0 \le g < 8$, $0 \le h < 8$ and $0 < g+h < 8$), a polyglycerol group of general formula (3)

(wherein $R^4$ is a substituted or unsubstituted monovalent hydrocarbon group or a hydrogen atom, and the subscripts l and i are integers which satisfy the conditions $0 \le l \le 15$ and $0 < i \le 5$) or $R^1$, with at least one $R^1$ being a polyoxyalkylene group of general formula (2) or a polyglycerol group of general formula 3; each $R^3$ is a like or unlike group of general formula (4), general formula (5), general formula (6) or general formula (7) below

[Chem. 8]

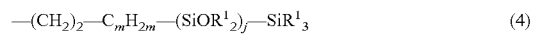

$$-(CH_2)_2-C_mH_{2m}-SiR^1{}_{k1}-(OSiR^1{}_{k2}(OSiR^1{}_3)_{3-k2})_{3-k1} \quad (6)$$

$$-(CH_2)_2-C_mH_{2m}-SiR^1{}_{k1}-(OSiR^1{}_{k2}(OSiR^1{}_{k3}(OSiR^1{}_3)_{3-k3})_{3-k2})_{3-k1} \quad (7)$$

(wherein $R^1$ is the same as above; and the subscripts m, j and k1 to k3 are integers which satisfy the conditions $0 \leq m \leq 5$, $0 \leq j \leq 500$, $0 \leq k1 \leq 2$, $0 \leq k2 \leq 2$ and $0 \leq k3 \leq 2$) or $R^1$, with at least one $R^3$ being a group of general formula (4), general formula (5), general formula (6) or general formula (7); and the subscripts a, b, c, d, e and f are numbers which satisfy the conditions $0 \leq a \leq 400$, $0 < b \leq 200$, $0 \leq c \leq 400$, $0 \leq d \leq 320$, $0 \leq e \leq 320$, $0 < f \leq 1,000$ and $0.5 \leq (a+b+c)/f \leq 1.5$].

In the above formula, each $R^1$ is a like or unlike alkyl, aryl or aralkyl group of 1 to 30 carbon atoms, or a halogen-substituted, amino-substituted or carboxyl-substituted group thereof. An alkyl group of 1 to 30 carbon atoms, aryl group of 6 to 30 carbon atoms, aralkyl group of 7 to 30 carbon atoms, or a halogen-substituted, amino-substituted or carboxyl-substituted group thereof is preferred. An alkyl group, fluorine-substituted alkyl group, chlorine-substituted alkyl group, amino-substituted alkyl group or carboxyl-substituted alkyl group of 1 to 10 carbon atoms, an aryl group of 6 to 10 carbon atoms or an aralkyl group of 7 to 10 carbon atoms is more preferred. Specific examples include methyl, ethyl, propyl, butyl, pentyl, cyclopentyl, cyclohexyl, phenyl, tolyl, trifluoropropyl, heptadecafluorodecyl, chloropropyl and chlorophenyl groups. Of these, an alkyl group of 1 to 5 carbon atoms, a phenyl group or a trifluoropropyl group is more preferred.

The subscript "a" satisfies the condition $0 \leq a \leq 400$, preferably $1 \leq a \leq 100$, and more preferably $1 \leq a \leq 50$. The subscript "b" satisfies the condition $0 \leq b \leq 200$, preferably $1 \leq b \leq 100$, more preferably $1 \leq b \leq 50$, and even more preferably $1 < b \leq 30$. When b is larger than 200, the melting point of the resin becomes low, resulting in a poor film formability. The subscript "c" satisfies the condition $0 \leq c \leq 400$, preferably $1 \leq c \leq 100$, more preferably $1 \leq c \leq 50$, and even more preferably $1 \leq c \leq 30$. When c is larger than 400, the melting point of the resin becomes low, similarly resulting in a poor film formability. The subscript "d" is a number which satisfies the condition $0 \leq d \leq 320$, the subscript "e" is a number which satisfies the condition $0 \leq e \leq 320$, the subscript "f" is a number which satisfies the condition $0 < f \leq 1,000$, and these subscripts are numbers which together satisfy the condition $0.5 \leq (a+b+c)/f \leq 1.5$, and preferably $0.7 \leq (a+b+c)/f \leq 1.2$.

Each $R^2$ is a like or unlike polyoxyalkylene group of general formula (2) below

[Chem. 9]

$$-(CH_2)_2-C_lH_{2l}-O-(C_2H_4O)_g(C_3H_6O)_hR^4 \quad (2)$$

(wherein $R^4$ is a substituted or unsubstituted monovalent hydrocarbon group or a hydrogen atom, and the subscripts l, g and h are integers which satisfy the conditions $0 \leq l \leq 15$, $0 \leq g < 8$, $0 \leq h < 8$ and $0 < g+h < 8$), a polyglycerol group of general formula (3)

[Chem. 10]

$$-(CH_2)_2-C_lH_{2l}-O-(CH_2CH(OH)CH_2O)_iR^4 \quad (3)$$

(wherein $R^4$ is a substituted or unsubstituted monovalent hydrocarbon group or a hydrogen atom, and the subscripts l and i are integers which satisfy the conditions $0 \leq l \leq 15$ and $0 < i \leq 5$) or $R^1$, with at least one $R^2$ being a polyoxyalkylene group of general formula (2) or a polyglycerol group of general formula (3).

If $R^2$ is a polyoxyalkylene group of general formula (2), a softer film forms; with an increase in the amount of polyoxyalkylene groups added, an even softer film forms. If $R^2$ is a polyglycerol group of general formula (3), a film having a toughness comparable with that of trimethylsiloxy-silicic acid forms.

$R^1$ is the same as above, and $R^4$ is a substituted or unsubstituted monovalent hydrocarbon group or a hydrogen atom. The subscript "l" satisfies the condition $0 \leq l \leq 15$, and preferably $0 \leq l \leq 2$. The subscript "i" satisfies the condition $0 < i \leq 5$, preferably $0 < i \leq 3$, and more preferably $0 < i \leq 2$. The subscript "g" satisfies the condition $0 \leq g < 8$, preferably $1 \leq g \leq 6$, and more preferably $1 \leq g \leq 5$. When g is larger than 8, the melting point of the resin becomes low, as a result of which the film formability worsens. The subscript "h" satisfies the condition $0 \leq h \leq 8$, preferably $0 \leq h \leq 6$, and more preferably $0 \leq h \leq 5$. When h is larger than 8, the melting point of the resin becomes low, as a result of which the film formability worsens. The sum g+h satisfies the condition $0 < g+h < 8$, preferably $1 \leq g+h \leq 6$, and more preferably $1 \leq g+h \leq 5$. When g+h is larger than 8, the melting point of the resin becomes low, as a result of which the film formability worsens. In cases where the polyoxyalkylene moiety consists of both ethylene oxide units and propylene oxide units, it may be either a block copolymer or a random copolymer of both these units.

Each $R^3$ is a like or unlike group of general formula (4), general formula (5), general formula (6) or general formula (7) below

[Chem. 11]

$$-(CH_2)_2-C_mH_{2m}-(SiOR^1{}_2)_j-SiR^1{}_3 \quad (4)$$

$$-(CH_2)_2-C_mH_{2m}-SiR^1{}_{k1}-(OSiR^1{}_3)_{3-k1} \quad (5)$$

$$-(CH_2)_2-C_mH_{2m}-SiR^1{}_{k1}-(OSiR^1{}_{k2}(OSiR^1{}_3)_{3-k2})_{3-k1} \quad (6)$$

$$-(CH_2)_2-C_mH_{2m}-SiR^1{}_{k1}-(OSiR^1{}_{k2}(OSiR^1{}_{k3}(OSiR^1{}_3)_{3-k3})_{3-k2})_{3-k1} \quad (7)$$

(wherein each $R^1$ is a like or unlike alkyl, aryl or aralkyl group of 1 to 30 carbon atoms, or a halogen-substituted group, amino-substituted group or carboxyl-substituted group thereof; and the subscripts m, j and k1 to k3 are integers which satisfy the conditions $0 \leq m \leq 5$, $0 \leq j \leq 500$, $0 \leq k1 \leq 2$, $0 \leq k2 \leq 2$ and $0 \leq k3 \leq 2$) or $R^1$, with at least one $R^3$ being a group of general formula (4), general formula (5), general formula (6) or general formula (7). Examples and preferred ranges for $R^1$ in these general formulas are the same as mentioned above. Also, the subscript "m" satisfies the condition $0 \leq m \leq 5$, and preferably $0 \leq m \leq 2$; and the subscript "j" satisfies the condition $0 \leq j \leq 500$, preferably $1 \leq j \leq 100$, and more preferably $1 \leq j \leq 50$. When the subscript "j" is larger than 500, the melting point of the resin becomes low, as a result of which the film formability worsens.

From the standpoint of reactions between vinyl groups and hydrogenpolysiloxanes, when synthesizing an entity of general formula (4), m is preferably 0. Also, when j is larger than 500, problems such as a worsening of the reactivity with main-chain hydrogenpolysiloxanes may arise, and so it is preferable for j to be within the above range. In addition, from the standpoint of reactions between vinyl groups and hydrogenpolysiloxanes, when synthesizing groups of general formulas (5), (6) and (7), m is preferably 0.

An organic group-modified organosilicon resin (i) wherein
the subscripts b and c in average compositional formula (1) satisfy the conditions $0 < b \leq 30$ and $0 \leq c \leq 30$;

if $R^2$ is a polyoxyalkylene group of general formula (2), subscripts g and h in general formula (2) are integers which satisfy the conditions $0 \leq g \leq 6$, $0 \leq h \leq 6$ and $0 < g+h \leq 6$;

if $R^2$ is a polyglycerol group of general formula (3), the subscript i in general formula (3) is an integer which satisfies the condition $0 < i \leq 3$; and if $R^3$ is a group of general formula (4), the subscript j in general formula (4) satisfies the condition $0 \leq j \leq 10$, is in the form of a solid, enabling an organic group-modified organosilicon resin to be obtained which has an even better film formability and forms a tough film that is not sticky.

Further restricting the conditions for the above organic group-modified organosilicon resin (i), an organic group-modified organosilicon resin (ii) wherein the subscripts b and c in average compositional formula (1) satisfy the conditions $0 < b \leq 30$ and $0 \leq c \leq 30$; the subscripts g and h in general formula (2) are integers which satisfy the conditions $0 \leq g \leq 5$, $0 \leq h \leq 5$ and $0 < g+h \leq 5$; the subscript i in general formula (3) is an integer which satisfies the condition $0 < i \leq 2$; and the subscript j in general formula (4) satisfies the condition $0 \leq j \leq 10$ is in the form of a solid, enabling an organic group-modified organosilicon resin to be obtained which has an even better film formability and has a particularly good solubility in silicone oils.

[Method of Preparation]

The organic group-modified organosilicon resin can be synthesized by various procedures already known in the technical field of the invention. For example, it is possible to introduce organic groups by silylating a chlorosilane such as $R^1SiCl$ (wherein $R^1$ is the same as above) onto the surface silanol groups of an organosilicon resin. However, given that complete control of the amount of silanol groups on the surface of the organosilicon resin is difficult, a problem with this approach is the difficulty of precisely controlling the amount of modifying organic groups. Also, because a strong acid forms during the silylation reaction, there is a possibility that this will break the organosilicon resin bonds. It is also possible to introduce organic functional groups by one-pot synthesis in which two types of alkoxysilanes consisting of Q units ($SiO_{4/2}$) and T units ($RSiO_{3/2}$) (some of the R moieties being organic functional groups) are subjected to co-condensation. However, because these two types of alkoxysilanes have differing hydrolyzabilities, it has been difficult to obtain an organosilicon resin in which the Q units and the T units are uniformly dispersed.

Hence, synthesis is generally carried out via a hydrosilylation reaction between an organosilicon resin having hydrosilyl groups as the reactive sites and a compound having alkenyl groups (carbon-carbon unsaturated bonds) at the ends.

The method for preparing the organic group-modified organosilicon resin of the invention includes the step of hydrosilylating a hydrosilyl group-containing organosilicon resin of average compositional formula (8) below

[Chem. 12]

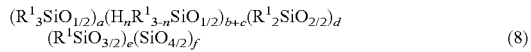

(wherein each $R^1$ is a like or unlike alkyl, aryl or aralkyl group of 1 to 30 carbon atoms, or a halogen-substituted group, amino-substituted group or carboxyl-substituted group thereof; the subscripts a, b, c, d, e, and f are integers which satisfy the conditions $0 \leq a \leq 400$, $0 < b \leq 200$, $0 \leq c \leq 400$, $0 \leq d \leq 320$, $0 \leq e \leq 320$, $0 < f \leq 1{,}000$ and $0.5 \leq (a+b+c)/f \leq 1.5$; and n is an integer that satisfies the condition $1 \leq n \leq 3$) with one or more compound that is selected from alkenyl group-terminated compounds of general formulas (9), (10), (11), (12), (13) and (14) below

[Chem. 13]

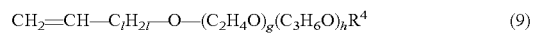 (9)

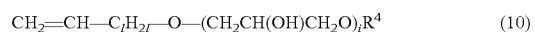 (10)

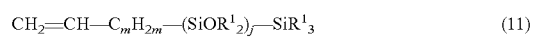 (11)

 (12)

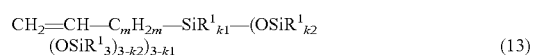 (13)

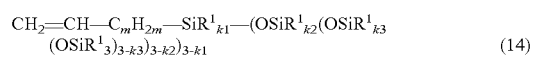 (14)

(wherein $R^4$ is a substituted or unsubstituted monovalent hydrocarbon group or a hydrogen atom, the subscripts l, g, h and i are integers which satisfy the conditions $0 \leq l \leq 15$, $0 \leq g < 8$, $0 \leq h < 8$, $0 < g+h < 8$ and $0 < i \leq 5$; and the subscripts m, j and k1 to k3 are integers which satisfy the conditions $0 \leq m \leq 5$, $0 \leq j \leq 500$, $0 \leq k1 \leq 2$, $0 \leq k2 \leq 2$ and $0 \leq k3 \leq 2$) and includes a compound of general formula (9) or (10), the compound of general formula (9) or (10) being essential. The hydrosilylation reaction is carried out in the presence of, for example, a platinum catalyst or a rhodium catalyst. Preferred ranges for b, c, d, e, f, $R^4$, l, g, h, m, i, j and k1 to k3 are as defined above.

[Hydrosilyl Group-Containing Organosilicon Resin Used as Starting Material]

The hydrosilyl group-containing organosilicon resin of average compositional formula (8) may be in a solid or liquid form at 25° C., although in terms of film formability, it is preferably a solid. From the standpoint of usefulness, the resin is preferably diluted with an organic solvent. The use of a solvent having a boiling point that is higher than the refluxing temperature during hydrolysis is preferred.

Examples of the organic solvent used in dilution include cyclic organopolysiloxanes such as octamethylcyclotetrasiloxane, decamethylcyclopentasiloxane and dodecamethylcyclohexasiloxane; aromatic hydrocarbons such as toluene and xylene; ketone-type organic solvents such as acetone, methyl ethyl ketone, diethyl ketone and methyl isobutyl ketone; aliphatic hydrocarbons such as hexane, heptane, octane and cyclohexane; and aliphatic alcohols such as methanol, ethanol, 1-propanol, 2-propanol, 1-butanol, 2-methyl-1-propanol, 2-butanol, 2-methyl-2-propanol, 1-pentanol, 2-methylbutanol, 2-pentanol, 1-hexanol, 2-methylpentanol, 1-heptanol, 1-octanol, 1-nonanol, 1-decanol, phenol, benzyl alcohol, ethylene glycol and 1,2-propylene glycol. From the standpoint of the shelf stability and non-volatility in particular, octamethylcyclotetrasiloxane and decamethylcyclopentasiloxane are preferred.

The hydrosilyl group-containing organosilicon resin of average compositional formula (8) is prepared by hydrolyzing, in the presence of an acidic catalyst, a mixture of one or more compound selected from organosilicon compounds of general formulas (15) and (16) below, one or more compound selected from among hydrosilyl group-containing organosilicon compounds of general formulas (17) and (18) below, and one or more compound selected from hydrolyzable silanes of general formula (19) below, partial hydrolytic condensates of such hydrolyzable silanes and metal salts of such hydrolyzable silanes

 (15)

$$R^1{}_3SiX^1 \quad (16)$$

$$H_nR^1{}_{(3-n)}SiOSiR^1{}_{(3-n)}H_n \quad (17)$$

$$H_nR^1{}_{(3-n)}SiX^2 \quad (18)$$

(wherein each $R^1$ is a like or unlike alkyl, aryl or aralkyl group of 1 to 30 carbon atoms, or a halogen-substituted group, amino-substituted group or carboxyl-substituted group thereof; $X^1$ and $X^2$ are hydrolyzable functional groups; and n satisfies the condition $1 \leq n \leq 3$)

$$SiX^3{}_4 \quad (19)$$

(wherein $X^3$ is a hydrolyzable functional group), neutralizing the reaction system by adding a basic catalyst in an amount greater than the molar equivalent of the acidic catalyst, and subsequently carrying out condensation.

In general formulas (15), (16), (17) and (18), examples of and the preferred range for $R^1$ are the same as mentioned above.

In general formula (16), $X^1$ is a hydrolyzable functional group that is directly bonded to a silicon atom. Examples include halogen atoms such as chlorine and bromine atoms, alkoxy groups such as methoxy, ethoxy, propoxy and butoxy groups, alkenoxy groups, acyloxy groups, amide groups and oxime groups. Of these, from the standpoint of availability and rate of hydrolysis, a methoxy group, an ethoxy group or a chlorine atom is preferred.

In general formula (18), $X^2$ is a hydrolyzable functional group that is directly bonded to a silicon atom. Examples include halogen atoms such as chlorine and bromine atoms, alkoxy groups such as methoxy, ethoxy, propoxy and butoxy groups, alkenoxy groups, acyloxy groups, amide groups and oxime groups. Of these, from the standpoint of availability and rate of hydrolysis, a methoxy group, an ethoxy group or a chlorine atom is preferred.

In general formula (19), $X^3$ is a hydrolyzable functional group that is directly bonded to a silicon atom. Examples include halogen atoms such as chlorine and bromine atoms, alkoxy groups such as methoxy, ethoxy, propoxy and butoxy groups, alkenoxy groups, acyloxy groups, amide groups and oxime groups. Of these, an alkoxy group is preferred; from the standpoint of availability and rate of hydrolysis, a methoxy group or an ethoxy group is preferred. The hydrolyzable groups $X^3$ on the molecule may be like or unlike groups.

Examples of organosilicon compounds of general formula (15) include 1,1,1,3,3,3-hexamethyldisiloxane, 1,1,1,3,3,3-hexaphenyldisiloxane, 1,1,3,3-tetramethyl-1,3-divinyldisiloxane, 1,1,1,3,3,3-hexaethyldisiloxane, 1,1,1,3,3,3-hexavinyldisiloxane, 1,1,1,3,3,3-pentavinylmethyldisiloxane, 1,1,1,3,3-n-octylpentamethyldisiloxane, 1,1,1,3,3-chloromethylpentamethyldiloxane, 1,1,3,3-tetramethyl-1,3-diallyldisiloxane and 1,3-dimethyl-1,1,3,3-tetravinyldisiloxane. Of these, 1,1,1,3,3,3-hexamethyldisiloxane and 1,1,1,3,3,3-hexaphenyldisiloxane are preferred.

Examples of organosilicon compounds of general formula (16) include trimethylchlorosilane, triethylchlorosilane, ethyldimethylchlorosilane, trivinylchlorosilane, dimethylvinylchlorosilane, triphenylchlorosilane, dimethylphenylchlorosilane, methyldiphenylchlorosilane, trimethylmethoxysilane, trimethylethoxysilane, triethylmethoxysilane, triethylethoxysilane, triphenylmethoxysilane and triphenylethoxysilane. Of these, trimethylchlorosilane and trimethylethoxysilane are preferred.

Examples of hydrosilyl group-containing organosilicon compounds of general formula (17) include 1,1,3,3-tetramethyldisiloxane and 1,1,1,3,3-pentamethyldisiloxane. 1,1,3,3-Tetramethyldisiloxane is especially preferred. Also, in general formulas (17) and (18), n satisfies the condition 1 n 3. In general formula (17), the "n" associated with the H and $R^1$ bonded to one silicone atom and the "n" associated with the H and $R^1$ bonded to the other silicon atom may be the same or different.

Examples of hydrosilyl group-containing organosilicon compounds of general formula (18) include dimethylchlorosilane, diphenylchlorosilane, dimethylmethoxysilane and dimethylethoxysilane. Dimethylchlorosilane and dimethylmethoxysilane are especially preferred.

Examples of the hydrolyzable silane of general formula (19) include tetrachlorosilane, tetramethoxysilane and tetraethoxysilane. Examples of partial hydrolytic condensates of the hydrolyzable silane include tetramethoxysilane condensates and tetraethoxysilane condensates. Examples of metal salts of the hydrolyzable silane include water glass, sodium silicate and potassium silicate. Tetraethoxysilane and tetraethoxysilane condensates are especially preferred.

In this invention, a mixture of one or more compound selected from organosilicon compounds of general formulas (15) and (16), one or more compound selected from hydrosilyl group-containing organosilicon compounds of general formulas (17) and (18) and one or more compound selected from hydrolyzable silanes of general formula (19), partial hydrolytic condensates of such hydrolyzable silanes and metal salts of such hydrolyzable silanes may be added prior to hydrolysis under an acidic catalyst, or a mixture of one or more compound selected from organosilicon compounds of general formula (20) or general formula (21)

$$R^1SiX^4{}_3 \quad (20)$$

$$R^1{}_2SiX^5{}_2 \quad (21)$$

(wherein each $R^1$ is a like or unlike alkyl, aryl or aralkyl group of 1 to 30 carbon atoms, or a halogen-substituted group, amino-substituted group or carboxyl-substituted group thereof; and $X^4$ and $X^5$ are hydrolyzable functional groups) may be added after such hydrolysis and prior to the subsequently described re-hydrolysis.

In general formulas (20) and (21), examples of and preferred ranges for $R^1$ are the same as mentioned above.

In general formula (20), $X^4$ is a hydrolyzable functional group that is directly bonded to a silicon atom. Examples include halogen atoms such as chlorine and bromine atoms, alkoxy groups such as methoxy, ethoxy, propoxy and butoxy groups, alkenoxy groups, acyloxy groups, amide groups and oxime groups. Of these, from the standpoint of availability and rate of hydrolysis, a methoxy group, an ethoxy group or a chlorine atom is preferred. The hydrolyzable groups $X^4$ on a single molecule may be like or unlike.

In general formula (21), $X^5$ is a hydrolyzable functional group that is directly bonded to a silicon atom. Examples include halogen atoms such as chlorine and bromine atoms, alkoxy groups such as methoxy, ethoxy, propoxy and butoxy groups, alkenoxy groups, acyloxy groups, amide groups and oxime groups. Of these, from the standpoint of availability and rate of hydrolysis, a methoxy group, an ethoxy group or a chlorine atom is preferred. The hydrolyzable groups $X^5$ on a single molecule may be like or unlike.

Examples of silicon compounds of general formula (20) include methyltrimethoxysilane, methyltriethoxysilane, ethyltrimethoxysilane, pentyltriethoxysilane, phenyltriethoxysilane, benzyltriethoxysilane, chloropropyltriethoxysilane, bromopropyltriethoxysilane, cyclohexyltrimethoxysilane, trifluoropropyltrimethoxysilane and methyltrichlorosilane.

Of these, methyltrimethoxysilane, methyltriethoxysilane and methyltrichlorosilane are preferred.

Examples of silicon compounds of general formula (21) include dimethyldimethoxysilane, dimethyldiethoxysilane, diethyldimethoxysilane, dipentyldiethoxysilane, diphenyldiethoxysilane, dibenzyldiethoxysilane, dichloropropyldiethoxysilane, dibromopropyldiethoxysilane, dicyclohexyldimethoxysilane, difluoropropyldimethoxysilane and dimethyldichlorosilane. Of these, dimethyldimethoxysilane, dimethyldiethoxysilane and dimethyldichlorosilane are preferred.

A specific example of a method for preparing the hydrosilyl group-containing organosilicon resin serving as a starting material in this invention is described. A solvent (in particular, an organic solvent) and a hydrolysis starting material (a mixture of one or more compound selected from organosilicon compounds of general formulas (15) and (16), one or more compound selected from hydrosilyl group-containing organosilicon compounds of general formulas (17) and (18), and one or more compound selected from hydrolyzable silanes of general formula (19), partial hydrolytic condensates of such hydrolyzable silanes and metal salts of such hydrolyzable silanes) are charged into a reactor, an acid is added as a catalyst, and water is added dropwise under stirring. It is also possible in this case to add the organic solvent after completing dropwise addition of the water. Because hydrolysis is preferably carried out under acidic conditions, the addition of an acidic catalyst is essential.

The temperature during dropwise addition of the water is preferably between 0 and 80° C., and more preferably between 0 and 50° C. By keeping the temperature within this range, the heat of reaction from the hydrolysis reaction on the hydrolysis starting material in the system can be held down. The amount of water added dropwise, expressed as a molar ratio per mole of hydrolyzable functional groups (alkoxy groups, etc.) is in the range of 0.6 to 2, and preferably 1.0 to 1.8. By holding the amount of water added within this range, it is possible to further suppress the deactivation of hydrosilyl groups.

In order to suppress a decrease in the reaction rate due to retention and increased viscosity of the uniform reaction system during the hydrolysis reaction, it is preferable to use an organic solvent as the solvent in the hydrolysis reaction. It is also desirable to use a solvent having a boiling point that is higher than the refluxing temperature during hydrolysis.

Examples of organic solvents include cyclic organopolysiloxanes such as octamethylcyclotetrasiloxane, decamethylcyclopentasiloxane and dodecamethylcyclohexasiloxane; aromatic hydrocarbons such as toluene and xylene; ketone-type organic solvents such as acetone, methyl ethyl ketone, diethyl ketone and methyl isobutyl ketone; and aliphatic hydrocarbons such as hexane, heptane, octane and cyclohexane.

In some cases, an alcohol solvent of 1 to 10 carbon atoms may be concomitantly used. Examples include methanol, ethanol, 1-propanol, 2-propanol, 1-butanol, 2-methyl-1-propanol, 2-butanol, 2-methyl-2-propanol, 1-pentanol, 2-methylbutanol, 2-pentanol, 1-hexanol, 2-methylpentanol, 1-heptanol, 1-octanol, 1-nonanol, 1-decanol, phenol, benzyl alcohol, ethylene glycol and 1,2-propylene glycol. Because alcohol solvents undergo alcohol exchange reactions with hydrolyzable groups such as alkoxy groups, the use of a long-chain alcohol solvent is rate-limiting on the hydrolysis reaction. Hence, methanol, ethanol, 1-propanol and 2-propanol are especially preferred.

The solvent used is included in an amount, based on the overall reaction system, of from 1 to 80% (here and below, "%" refers to percent by weight), and especially 5 to 50%. Within this range, the reaction system is kept uniform and the reaction proceeds efficiently.

Examples of acidic catalysts include hydrochloric acid, sulfuric acid, sulfurous acid, fuming sulfuric acid, oxalic acid, p-toluenesulfonic acid, methanesulfonic acid, trifluoromethanesulfonic acid, phosphoric acid, formic acid, acetic acid, propionic acid, benzoic acid and citric acid. The acidic catalyst may be used in a small amount, with an amount in the range of 0.001 to 10% of the overall reaction system being preferred.

After water has been added dropwise as mentioned above, the hydrolysis reaction is carried out by heating the system at a temperature of between 50 and 150° C., preferably between 80 and 120° C., for about 2 to 8 hours. At this time, by carrying out the reaction at below the boiling point of the hydrosilyl group-containing organic compound used, deactivation of the hydrosilyl groups can be further suppressed.

After hydrolysis has been carried out in this way on the above hydrolysis starting material in the presence of an acidic catalyst, the system is cooled to between 10 and 100° C., preferably between 10 and 60° C., more preferably between 10 and 30° C., and even more preferably to 25° C.

Following the above hydrolysis, the system is neutralized at between 10 and 40° C. with a basic catalyst such as an alkali metal carbonate, an alkali metal bicarbonate or an alkali metal hydroxide. At this time, by using together a strong basic catalyst and a weak basic catalyst, hydrosilyl group deactivation is suppressed and the organosilicon resin condensation reaction is further promoted. Examples of such strong basic catalysts include lithium hydroxide, sodium hydroxide, potassium hydroxide, calcium hydroxide and barium hydroxide. Examples of weak basic catalysts include sodium carbonate, calcium carbonate and sodium bicarbonate. In terms of combinations of a strong basic catalyst with a weak basic catalyst, from the standpoint of the ease of achieving a high molecular weight, a combination of sodium hydroxide and calcium carbonate is desirable. With this combination, the molecular weight rises sufficiently, enabling a high-molecular-weight hydrosilyl group-containing organosilicon resin to be more reliably obtained.

The basic catalyst must be used in an amount that is larger than the molar equivalent of the acidic catalyst. Carrying out neutralization with an amount of basic catalyst that is larger than the molar equivalent of the acidic catalyst favors the organosilicon resin condensation reaction, as a result of which the molecular weight rises, enabling a high-molecular-weight hydrosilyl group-containing organosilicon resin to be obtained. The amount of basic catalyst used is preferably in the range of 1.0 to 3.0 molar equivalent of the acidic catalyst. Setting the amount of addition within this range favors the hydrosilyl group-containing organosilicon resin condensation reaction, enabling a resin of the target molecular weight to be obtained.

Following neutralization, the alcohols that have formed, the solvent and excess water may be driven off by heating at between 95 and 120° C. under normal pressure or reduced pressure. Next, after confirming that the formed alcohols, solvent and excess water have been driven off, the condensation reaction is carried out by heating at between 120 and 150° C. for about 2 to 5 hours. A hydrosilyl group-containing organosilicon resin is thereby obtained.

In the above-described method for preparing a hydrosilyl group-containing organosilicon resin, the ratio between the combined molar amount of the compounds of general formulas (15), (16), (17) and (18) and the molar amount of $SiO_{4/2}$ units in the compound of general formula (19), expressed as the molar ratio ((15)+(16)+(17)+(18)):(19), is preferably from 0.3:1 to 2:1, and more preferably from 0.6:1 to 1.3:1. In addition, the ratio between the combined molar amount of the compounds of general formulas (15) and (16) and the combined molar amount of the compounds of general formulas (17) and (18), expressed as the molar ratio ((15)+(16)):((17)+(18)), is preferably from 0.3:1.0 to 2.0:1.0, and more preferably from 0.6:1.0 to 1.3:1.0. By setting the values within these ranges, the amount of hydrosilyl groups included in the hydrosilyl group-containing organosilicon resin can be quantitatively varied more precisely. In this invention, by thus varying the amounts in which the compounds of general formulas (17) and (18) are charged, it is possible to quantitatively vary the amount of hydrosilyl groups included on the organosilicon resin.

In the above-described method for preparing a hydrosilyl group-containing organosilicon resin, after carrying out the hydrolysis, in the presence of an acidic catalyst, of a mixture of one or more compound selected from organosilicon compounds of general formulas (15) and (16) with one or more compound selected from hydrolyzable silanes of general formula (19), partial hydrolytic condensates of such hydrolyzable silanes and metal salts of such hydrolyzable silanes, it is possible to also gradually add dropwise one or more compound selected from hydrosilyl group-containing organosilicon compounds of general formulas (17) and (18).

Next, re-hydrolysis is carried out. At this time, the re-hydrolysis reaction is preferably carried out by heating at below the boiling point of the hydrosilyl group-containing organosilicon compound, such as to a temperature of preferably between 40 and 150° C., and more preferably between 40 and 120° C., for about 2 to 8 hours. When the reaction is carried out within this temperature range, deactivation of the hydrosilyl groups can be further suppressed.

In the method for preparing the hydrosilyl group-containing organosilicon resin, the reaction of formula (22) below, wherein some of the hydrosilyl groups deactivate, may arise.

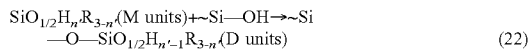

$$\mathrm{SiO}_{1/2}\mathrm{H}_n\mathrm{R}_{3-n}\text{(M units)} + \sim\!\mathrm{Si}\!-\!\mathrm{OH} \rightarrow \sim\!\mathrm{Si}\!-\!\mathrm{O}\!-\!\mathrm{SiO}_{1/2}\mathrm{H}_{n'-1}\mathrm{R}_{3-n}\text{(D units)} \quad (22)$$

Here, R is a monovalent hydrocarbon group of 1 to 10 carbon atoms, and n' is an integer from 1 to 3.

However, by suitably setting the order in which the starting materials are added, that is, by hydrolyzing a mixture of one or more compound selected from organosilicon compounds of general formulas (15) and (16) with one or more compound selected from hydrolyzable silanes of general formula (19), partial hydrolytic condensates of such hydrolyzable silanes and metal salts of such hydrolyzable silanes, and subsequently adding one or more compound selected from hydrosilyl group-containing organosilicon compounds of general formulas (17) and (18) and carrying out re-hydrolysis, above reaction (22) can be held to a minimum. This reaction can be further suppressed by artfully modifying the amounts in which the starting materials are added and the type of catalyst used.

The amount of hydrosilyl groups included in the hydrosilyl group-containing organosilicon resin thus obtained is easily adjustable, and it is even possible to introduce a large amount of hydrosilyl groups, by varying the amount of the hydrosilyl group-containing organosilicon compound that is charged. In addition, by varying the amount of hydrolysis starting materials used, the type and amount of acidic catalyst added, the reaction temperature and time, the amount of solvent added and the method of addition, the molecular weight range, shape and other characteristics of the organosilicon resin can be adjusted, in this way making it possible to prepare a hydrosilyl group-containing organosilicon resin for the intended application.

The hydrosilyl group-containing organosilicon resin obtained as described above has average compositional formula (8) above and is composed of Q units ($\mathrm{SiO}_{4/2}$) and M units (($\mathrm{R}^1_3\mathrm{SiO}_{1/2}$) and ($\mathrm{H}_n\mathrm{R}^1_{3-n}\mathrm{SiO}_{1/2}$)) as essential constituents, and also D units ($\mathrm{R}^1_2\mathrm{SiO}_{2/2}$) and T units ($\mathrm{R}^1\mathrm{SiO}_{3/2}$) as optional constituents. It may be in the form of a solid or a liquid at 25° C., although from the standpoint of film formability, it is preferably a solid. Examples include MQ resins, MTQ resins, MDQ resins and MDTQ resins. The weight-average molecular weight is preferably in the range of 2,000 to 30,000, although the range of 3,000 to 15,000 is more preferred from the standpoint of performance and ease of carrying out operations such as filtration. The weight-average molecular weight can be determined as the polystyrene-equivalent weight-average molecular weight in gel permeation chromatography (GPC).

[Method for Preparing Organic Group-Modified Organosilicon Resin]

A specific example of a method for preparing the organic group-modified organosilicon resin in this invention is described below.

As mentioned above, the organic group-modified organosilicon resin of the invention can be obtained by the step of hydrosilylating a hydrosilyl group-containing organosilicon resin of average compositional formula (8) below

[Chem. 14]

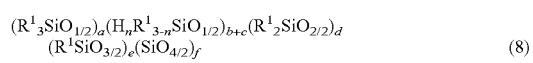

$$(\mathrm{R}^1_3\mathrm{SiO}_{1/2})_a(\mathrm{H}_n\mathrm{R}^1_{3-n}\mathrm{SiO}_{1/2})_{b+c}(\mathrm{R}^1_2\mathrm{SiO}_{2/2})_d (\mathrm{R}^1\mathrm{SiO}_{3/2})_e(\mathrm{SiO}_{4/2})_f \quad (8)$$

(wherein each $\mathrm{R}^1$ is a like or unlike alkyl, aryl or aralkyl group of 1 to 30 carbon atoms, or a halogen-substituted group, amino-substituted group or carboxyl-substituted group thereof; the subscripts a, b, c, d, e, and f are integers which satisfy the conditions $0 \leq a \leq 400$, $0 < b \leq 200$, $0 \leq c \leq 400$, $0 \leq d \leq 320$, $0 \leq e \leq 320$, $0 < f \leq 1{,}000$ and $0.5 \leq (a+b+c)/f \leq 1.5$; and n is an integer that satisfies the condition $1 \leq n \leq 3$) with one or more compound that is selected from alkenyl group-terminated compounds of general formulas (9), (10), (11), (12), (13) and (14) below

[Chem. 15]

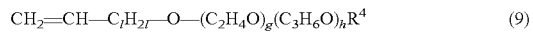

$$\mathrm{CH}_2\!=\!\mathrm{CH}\!-\!\mathrm{C}_l\mathrm{H}_{2l}\!-\!\mathrm{O}\!-\!(\mathrm{C}_2\mathrm{H}_4\mathrm{O})_g(\mathrm{C}_3\mathrm{H}_6\mathrm{O})_h\mathrm{R}^4 \quad (9)$$

$$\mathrm{CH}_2\!=\!\mathrm{CH}\!-\!\mathrm{C}_l\mathrm{H}_{2l}\!-\!\mathrm{O}\!-\!(\mathrm{CH}_2\mathrm{CH(OH)}\mathrm{CH}_2\mathrm{O})_i\mathrm{R}^4 \quad (10)$$

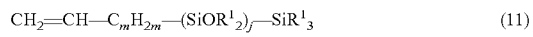

$$\mathrm{CH}_2\!=\!\mathrm{CH}\!-\!\mathrm{C}_m\mathrm{H}_{2m}\!-\!(\mathrm{SiOR}^1_2)_j\!-\!\mathrm{SiR}^1_3 \quad (11)$$

$$\mathrm{CH}_2\!=\!\mathrm{CH}\!-\!\mathrm{C}_m\mathrm{H}_{2m}\!-\!\mathrm{SiR}^1_{k1}\!-\!(\mathrm{OSiR}^1_3)_{3-k1} \quad (12)$$

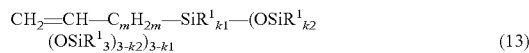

$$\mathrm{CH}_2\!=\!\mathrm{CH}\!-\!\mathrm{C}_m\mathrm{H}_{2m}\!-\!\mathrm{SiR}^1_{k1}\!-\!(\mathrm{OSiR}^1_{k2}(\mathrm{OSiR}^1_3)_{3-k2})_{3-k1} \quad (13)$$

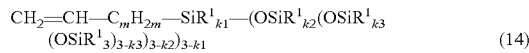

$$\mathrm{CH}_2\!=\!\mathrm{CH}\!-\!\mathrm{C}_m\mathrm{H}_{2m}\!-\!\mathrm{SiR}^1_{k1}\!-\!(\mathrm{OSiR}^1_{k2}(\mathrm{OSiR}^1_{k3}(\mathrm{OSiR}^1_3)_{3-k3})_{3-k2})_{3-k1} \quad (14)$$

(wherein $\mathrm{R}^4$ is a substituted or unsubstituted monovalent hydrocarbon group or a hydrogen atom, the subscripts l, g, h and i are integers which satisfy the conditions $0 \leq l \leq 15$, $0 \leq g \leq 8$, $0 \leq h \leq 8$, $0 < g+h \leq 8$ and $0 < i \leq 5$; and the subscripts m, j and k1 to k3 are integers which satisfy the conditions $0 \leq m \leq 5$, $0 \leq j \leq 500$, $0 \leq k1 \leq 2$, $0 \leq k2 \leq 2$ and $0 \leq k3 \leq 2$) and includes a compound of general formula (9) or (10). The hydrosilyl group-containing organosilicon resin of average compositional formula (8) and the compound having terminal alkenyl groups of general formula (9), (10), (11), (12), (13) or (14) are mixed in a molar ratio, expressed as hydrosilyl groups/terminal unsaturated groups, which is preferably from 0.5 to 2.0, and more preferably from 0.8 to 1.2.

The addition reaction is preferably carried out in the presence of a platinum catalyst or a rhodium catalyst. Specific examples include chloroplatinic acid, alcohol-modified chloroplatinic acid and chloroplatinic acid-vinyl siloxane complexes. When an excessive amount of the catalyst is included, sample discoloration occurs, and so the amount of platinum or rhodium is preferably 50 ppm or less, and more preferably 20 ppm or less.

In addition, where necessary, the addition reaction may be carried out in the presence of an organic solvent. Examples of the organic solvent include cyclic organopolysiloxanes such as octamethylcyclotetrasiloxane, decamethylcyclopentasiloxane and dodecamethylcyclohexasiloxane; aromatic hydrocarbons such as toluene and xylene; ketone-type solvents such as acetone, methyl ethyl ketone, diethyl ketone and methyl isobutyl ketone; aliphatic hydrocarbons such as hexane, heptane, octane and cyclohexane; and aliphatic alcohols such as methanol, ethanol, 1-propanol, 2-propanol, 1-butanol, 2-methyl-1-propanol, 2-butanol, 2-methyl-2-propanol, 1-pentanol, 2-methylbutanol, 2-pentanol, 1-hexanol, 2-methylpentanol, 1-heptanol, 1-octanol, 1-nonanol, 1-decanol, phenol, benzyl alcohol, ethylene glycol and 1,2-propylene glycol. From the standpoint of reactivity, ethanol, 1-propanol and 2-propanol are preferred.

The amount of solvent used is preferably from 1 to 80%, and more preferably from 5 to 50%, of the overall reaction system. Within the above range, the reaction system is held uniform and the reaction proceeds efficiently.

The addition reaction conditions are not particularly limited, although heating under refluxing at a temperature between 50 and 150° C., especially between 80 and 120° C., for about 1 to 10 hours is preferred.

Following the addition reaction, the step of removing the rhodium catalyst or platinum catalyst used with activated carbon may be included. The amount of activated carbon used is preferably from 0.001 to 5.0%, and especially from 0.01 to 1.0%, of the overall system. By setting the amount of activated carbon within this range, sample discoloration can be better suppressed.

Following the addition reaction, if necessary, the step of removing remaining hydrosilyl groups may be included. Particularly in cases where use in applications such as cosmetic preparations is intended, there is a possibility of such hydrosilyl groups deactivating over time due to dehydrogenation reactions, which poses a problem from the standpoint of safety. Hence, it is preferable to include a hydrosilyl group-remaining step.

An example of a hydrosilyl group-removing step is the process of hydrolyzing unreacted hydrosilyl groups by adding a basic catalyst such as an alkali metal carbonate, alkali metal bicarbonate or alkali metal hydroxide, and subsequently neutralizing by adding an amount of an acidic catalyst equal to the molar equivalent of the basic catalyst. Specific examples of the basic catalyst include strong basic catalysts such as lithium hydroxide, sodium hydroxide, potassium hydroxide, calcium hydroxide and barium hydroxide; and weak basic catalysts such as sodium carbonate, calcium carbonate and sodium bicarbonate. From the standpoint of promoting the dehydrogenation reaction, the use of a strong basic catalyst is especially preferred, with sodium hydroxide being especially preferred. Examples of acidic catalysts include hydrochloric acid, sulfuric acid, sulfurous acid, fuming sulfuric acid, oxalic acid, p-toluenesulfonic acid, methanesulfonic acid, trifluoroacetic acid, trifluoromethanesulfonic acid, phosphoric acid, formic acid, acetic acid, propionic acid, benzoic acid and citric acid. Generally, instead of using the acid or base alone, it is preferable to use it together with water and to heat it at a temperature that is no higher than the boiling point of water.

Following the addition reaction, if necessary, a deodorizing step to reduce odor may be included. When use in applications such as cosmetic preparations in particular is intended, because the product acquires an odor over time, it is preferable to include a deodorizing step. The deodorizing mechanism for common polyether-modified silicones can be explained as follows. When an addition reaction between an allyl-etherified polyether and a hydrogen polyorganosiloxane is carried out in the presence of a platinum catalyst, allyl groups internally rearrange as side reactions, forming a propenyl-etherified polyether. This propenyl-etherified polyether has no reactivity with hydrogen polyorganosiloxane, and so remains behind in the system as an impurity. It is thought that when water acts on this propenyl-etherified polyether, the propenyl ether hydrolyzes, giving rise to propionaldehyde, which gives off an unpleasant odor. The above hydrolysis reaction is known to be further promoted in the presence of an acidic catalyst. Hence, when the polyether-modified silicone is used in a water-based cosmetic preparation, due to oxidative deterioration of the polyether, the preparation tends to become acidic over time, promoting the hydrolysis reaction described above and causing an off-odor to arise.

Typical examples of the deodorizing step include two approaches. The first is one in which, by adding an acidic catalyst to the solution following the addition reaction, all of the propenyl ether remaining in the system is hydrolyzed and the propionaldehyde that forms is removed by strip purification (JP No. 2137062).

Specific examples of the acidic catalyst used in the first approach include hydrochloric acid, sulfuric acid, sulfurous acid, fuming sulfuric acid, oxalic acid, p-toluenesulfonic acid, methanesulfonic acid, trifluoroacetic acid, trifluoromethanesulfonic acid, phosphoric acid, formic acid, acetic acid, propionic acid, benzoic acid and citric acid. These acids are used in combination with water. In cases where there is a need to remove acid that was used, it is preferable to use an acid having a low boiling point, such as hydrochloric acid, formic acid, acetic acid or trifluoroacetic acid. Also, from the standpoint of treatment efficiency, it is preferable to use a strong acid such as hydrochloric acid or trifluoroacetic acid.

The treatment temperature is preferably set to 80° C. or below in order to prevent the oxidation of hydrophilic groups. The amount of acidic aqueous solution added is preferably set to from 0.1 to 100% with respect to the organic group-modified organosilicon resin. The use of 5 to 30% is more preferred.

From the standpoint of productivity, the method of adding to the post-reaction solution an aqueous solution such as to set the pH to 7 or below and carrying out strip purification after stirring under heating is preferred. The strip purification may be carried out at normal temperature or may be carried out under reduced pressure. The temperature conditions are preferably set to 120° C. or less. In order to efficiently strip purify under these temperature conditions, it is preferable to carry out this operation under reduced pressure; when carried out at normal pressure, the operation is preferably carried out under a stream of inert gas such as nitrogen or argon.

The second approach is one in which, by adding hydrogen to the solution following the addition reaction, unsaturated double bonds are alkylated (subjected to a hydrogenation reaction) and the formation of propionaldehyde over time is stably controlled (U.S. Pat. No. 5,225,509; JP-A H07-330907).

Hydrogenation reactions include methods involving the use of hydrogen and methods involving the use of metal hydrides, and there are also homogeneous reactions and heterogeneous reactions. These may be used alone, although it is also possible to use them in combination. However, given the advantage that none of the catalyst used remains in the product, a heterogeneous catalytic hydrogenation reaction using a solid catalyst is preferred.

The solid catalyst is exemplified by nickel, palladium, platinum, rhodium, cobalt, chromium, copper, iron and the like, either in uncombined form or as a compound thereof. There need not be a catalyst support in this case. However, when a catalyst support is used, the support may be, for example, activated carbon, silica, silica alumina, alumina or zeolite. These catalysts may be used alone, although it is also possible to use them in combination. The preferred catalyst is the economically advantageous Raney nickel. Because Raney nickel is generally developed and used with an alkali, there is a need to carefully measure the pH of the reaction system. Also, the reaction system becomes weakly alkaline, and so this is particularly effective for deodorization when the hydrolysis reaction is carried out with an acidic aqueous solution.

It is preferable to carry out the hydrogenation reaction at generally from 1 to 100 MPa and between 50 and 200° C. The hydrogenation reaction may be carried out as a batchwise process or as a continuous process. When it is a batchwise process, the reaction time depends on, for example, the amount of catalyst and the temperature, but is generally from 3 to 12 hours. The hydrogen pressure can be adjusted to a suitable fixed pressure. The endpoint of the hydrogenation reaction is the point at which the hydrogen pressure has stopped changing, and so it can be determined by carefully monitoring a pressure gage.

The amount of aldehyde included in the organic group-modified organosilicon resin that has been purified by such acid treatment and hydrogenation treatment can be set to 70 ppm or less, preferably 20 ppm or less, and more preferably 10 ppm or less.

It is also possible to combine the two types of deodorizing steps mentioned above. In the approach that involves acid treatment, decomposition and removal of the aldehyde compound is possible, but because there is a limit to the complete removal of unsaturated double bonds, the formation of odor-causing aldehyde from this cannot be completely suppressed. In the approach that involves a hydrogenation reaction, by eliminating unsaturated double bonds, it is possible to reduce the amount of aldehyde compound that forms on account of this. However, aldehyde condensate that forms with the condensation of some of the aldehyde remains within the system even after such treatment has been carried out and removal by strip purification is also difficult. Hence, by alkylating the unsaturated double bonds that remain behind when the solution following the addition reaction is subjected to hydrogenation, and subsequently decomposing aldehyde condensate within the system by adding an acidic catalyst, complete deodorization is possible (WO 2002/05588).

[Properties of Organic Group-Modified Organosilicon Resin]

The weight-average molecular weight of the organic group-modified organosilicon resin of average compositional formula (1) is preferably in the range of 1,000 to 100,000; from the standpoint of performance and ease of operations such as filtration, the weight-average molecular weight is more preferably in the range of 3,000 to 50,000. Here and below, the weight-average molecular weight can be determined as the polystyrene-equivalent weight-average molecular weight in gel permeation chromatography (GPC).

The organic group-modified organosilicon resin is in a form at 25° C. that may be solid or may be liquid, from the standpoint of film formability, it is preferably solid. In particular, the organic group-modified organosilicon resin (i) for which the subscripts b and c in average compositional formula (1) satisfy the conditions $0<b\leq30$ and $0\leq c\leq30$, the subscripts g and h in general formula (2) are integers which satisfy the conditions $0\leq g\leq6$, $0\leq h\leq6$ and $0<g+h\leq6$, the subscript i in general formula (3) is an integer which satisfies the condition $0<i\leq3$ and the subscript j in general formula (4) satisfies the condition $0\leq j\leq10$, and the organic group-modified organosilicon resin (ii) for which the subscripts h and c in average compositional formula (1) satisfy the conditions $0<b\leq30$ and $0\leq c\leq30$, the subscripts g and h in general formula (2) are integers which satisfy the conditions $0\leq g\leq5$, $0\leq h\leq5$ and $0<g+h\leq5$, the subscript i in general formula (3) is an integer which satisfies the condition $0<i\leq2$ and the subscript j in general formula (4) satisfies the condition $0\leq j\leq10$ are each in the form of a solid at 25° C. and have a weight-average molecular weight that is preferably in the range of 1,000 to 100,000 and more preferably, from the standpoint of performance and ease of operations such as filtration, in the range of 3,000 to 50,000.

Because the above organic group-modified organosilicon resin (i) and organic group-modified organosilicon resin (ii) are each in the form of a solid at 25° C., it is possible to use them as film-forming agents. The organosilicon resin prior to modification forms a strong film that is brittle, whereas the organic group-modified organosilicon resin following modification forms a tough film in which such brittleness is ameliorated and which is softer than a trimethylsiloxysilicic acid film and is not sticky. This is presumably because the organosilicon resin prior to modification forms a tough film but the film strength decreases upon modification with low-melting polyether groups or silicone.

Compared with prior to modification, the film formed of the organic group-modified organosilicon resin has a greatly increased resistance to oils such as sebum. The reason is thought to be that the modifying groups are hydrophilic groups such as polyether groups and polyglycerol groups that have a low solubility in oils—which are hydrophobic, and thus repel such oils.

In addition, by including the organic group-modified organosilicon resin as a film-forming agent in a cosmetic preparation, cosmetic preparations which are not sticky at the time of application, have an excellent feel on use, have good water and oil resistances, and have good adhesion to the skin and thus an excellent long-lasting performance can be obtained.

The organic group-modified organosilicon resin has a hydrophilic-lipophilic balance (HLB), as determined by Griffin's formula, of preferably from 0.1 to 15, and more preferably from 1.0 to 8.0.

[Cosmetic Preparation]

The organic group-modified organosilicon resin (A) of the invention can be used in various types of applications, with use as an ingredient in all cosmetic preparations intended for external use on the skin and hair in particular being possible. In such cases, the content of the organic group-modified organosilicon resin (A) is preferably from 0.1 to 40%, more preferably from 0.2 to 30%, and most preferably from 0.5 to 15%, of the overall cosmetic preparation. At less than 0.1%, a sufficient oil resistance is not obtained; at more than 40%, the feel on use worsens.

[Other Ingredients]

Various ingredients used in conventional cosmetic preparations may be included in the cosmetic preparation of the invention. Such other ingredients include, for example, (B) oils, (C) powders, (D) surfactants, (E) crosslinked organopolysiloxanes, (F) film-forming agents other than component (A), (G) aqueous ingredients, (H) waxes and (I) other additives. These may be used singly or two or more may be used in suitable combination. These ingredients are suitably selected and used according to the type of cosmetic preparation, and the contents thereof may be set to known contents suited to, for example, the type of cosmetic preparation.

(B) Oils

The oils may be ones that are solid, semisolid or liquid at room temperature. Examples include silicone oils, natural plant and animal oils and fats and semi-synthetic oils and fats, hydrocarbon oils, higher alcohols, fatty acids, ester oils and fluorocarbon oils. When an oil is included, the oil content, although not particularly limited, is preferably from 1 to 85%, and more preferably from 15 to 40%, of the overall cosmetic preparation.

Silicone Oils

Silicone oils are not particularly limited, provided that they are ingredients which can be included in conventional cosmetic preparations. Examples include low-viscosity to high-viscosity, linear or branched organopolysiloxanes such as dimethylpolysiloxane, decamethylcyclopentasiloxane, dodecamethylcyclohexasiloxane, disiloxane, trisiloxane, methyl trimethicone, capryl methicone, methyl phenyl polysiloxane, methyl hexyl polysiloxane, methyl hydrogen polysiloxane and dimethyl siloxane-methyl phenyl siloxane copolymers; amino-modified organopolysiloxanes, pyrrolidone-modified organopolysiloxanes, pyrrolidone carboxylic acid-modified organopolysiloxanes, silicone rubbers such as gum-like dimethyl polysiloxanes, gum-like amino-modified organopolysiloxanes and gum-like dimethylsiloxane-methyl phenyl siloxane copolymers having a high degree of polymerization, cyclic organopolysiloxane solutions of silicone gums and rubbers, trimethylsiloxysilicic acid, cyclic siloxane solutions of trimethylsiloxysilicic acid, higher alkoxy-modified silicones such as stearoxy silicone, higher fatty acid-modified silicones, alkyl-modified silicones, long-chain alkyl-modified silicones, amino acid-modified silicones, fluorine-modified silicones, silicone resins and dissolved silicone resins. Of these, volatile silicones that enable a light feel on use to be obtained, low-viscosity silicones (including commercial products available from Shin-Etsu Chemical Co., Ltd., such as TMF-1.5, KF-995, KF-96A-2cs and KF-96A-6cs), phenyl silicones used for increasing compatibility with other oils or for luster (including commercial products available from Shin-Etsu Chemical Co., Ltd., such as KF-56A and 54HV), and silicone waxes used for luster or to adjust the feel on use (including commercial products available from Shin-Etsu Chemical Co., Ltd., such as KP-561P, 562P and KF-7020S) are preferably used. One or more of these silicone oils may be used.

Natural Plant and Animal Fats and Oils and Semi-Synthetic Fats and Oils

Examples of natural plant and animal fats and oils and semi-synthetic fats and oils include avocado oil, linseed oil, almond oil, Chinese wax, perilla oil, olive oil, cocoa butter, kaya oil, cod liver oil, beef tallow, neatsfoot oil, beef bone fat, hydrogenated beef tallow, apricot kernel oil, hydrogenated oil, wheat germ oil, sesame oil, rice germ oil, rice bran oil, camellia kissi oil, safflower oil, shea butter, Chinese paulownia oil, cinnamon oil, turtle oil, soybean oil, tea oil, camellia Japonica seed oil, evening primrose oil, corn oil, lard, rapeseed oil, Japanese paulownia oil, germ oil, horse fat, persic oil, palm oil, palm kernel oil, castor oil, hydrogenated castor oil, castor oil fatty acid methyl ester, sunflower oil, grapeseed oil, jojova oil, macademia nut oil, mink oil, meadowfoam seed oil, cottonseed oil, coconut oil, hydrogenated coconut oil, glyceryl tricocoate, mutton tallow, peanut oil, lanolin, liquid lanolin, reduced lanolin, lanolin alcohol, hydrogenated lanolin, acetylated lanolin, acetylated lanolin alcohol, isopropyl lanolate, POE lanolin alcohol ethers, POE lanolin alcohol acetates, polyethylene glycol lanolate, POE hydrogenated lanolin alcohol ethers and egg yolk oil. Here, "POE" stands for polyoxyethylene.

Hydrocarbon Oils

Hydrocarbon oils are exemplified by linear, branched, and volatile hydrocarbon oils. Specific examples include hydrogenated polydecene, hydrogenated polybutene, liquid paraffin, light isoparaffin, isododecane, isohexadecane, light liquid isoparaffin, squalane, synthetic squalane, vegetable squalane, squalene and $C_{13-15}$ alkanes.

Higher Alcohols

Higher alcohols are exemplified by alcohols having 12 to 22 carbon atoms. Examples include lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol, 2-decyltetradecynol, cholesterol phytosterol, POE cholesterol ether, monostearyl glycerol ether (batyl alcohol) and monooleyl glyceryl ether (selachyl alcohol).

Fatty Acids

Examples of fatty acids include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid and 12-hydroxystearic acid.

Ester Oils

Examples of ester oils include diisobutyl adipate, 2-hexyldecyl adipate, di-2-heptylundecyl adipate, N-alkyl glycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dioctanoate, neopentyl glycol diheptanoate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, ethylhexyl isononanoate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, isopropyl lauroyl sarcosinate, diisostearyl malate, triethylhexanoin, $C_{12-15}$ alkyl benzoates, glyceryl tri(caprylate/caprate), cocoalkyl (caprylate/caprate), isodecyl neopentanoate, hexyl laurate, dicaprylyl carbonate, diisostearyl malate and diisopropyl adipate.

Fluorocarbon Oils

Examples of fluorocarbon oils include perfluoropolyether, perfluorodecalin and perfluorooctane.

(C) Powders

The powders are not particularly limited, provided they are ingredients which can be included in conventional cosmetic preparations. Examples include pigments and spherical silicone powders. When a powder is included, the powder content is not particularly limited, although it is desirable to include the powder in an amount of from 0.1 to 90%, and preferably from 1 to 35%, of the overall cosmetic preparation.

Pigments

The pigments are not particularly limited, so long as they are ones that generally can be used in makeup cosmetics. Examples include inorganic pigments such as talc, mica, kaolin, silica, calcium carbonate, zinc oxide, titanium oxide, red iron oxide, yellow iron oxide, black iron oxide, ultramarine, Prussian blue, carbon black, titanium suboxide, cobalt violet, chromium oxide, chromium hydroxide, cobalt titanate, bismuth oxychloride and titanium-mica pearlescent pigments; organic pigments such as zirconium, barium or aluminum lakes, including Red No. 201, Red No. 202, Red No. 204, Red No. 205, Red No. 220, Red No. 226, Red No. 228, Red No. 405, Orange No. 203, Yellow No. 205, Yellow No. 4, Yellow No. 5, Blue No. 1, Blue No. 404 and Green No. 3; natural pigments such as chlorophyll and n-carotene; and dyes. Use can also be made of pigments that have been rendered hydrophobic with silicones, esters, amino acids, fluorine or the like. Specific examples of hydrophobized inorganic powders include hydrophobized titanium oxide and hydrophobized iron oxide (commercial products include KTP-09W, 09Y, 09R and 09B from Shin-Etsu Chemical Co., Ltd.), dispersions containing hydrophobized microparticulate titanium oxide or hydrophobized microparticulate zinc oxide (commercial products include SPD-T5, T6, T5L, Z5, Z6 and Z5L from Shin-Etsu Chemical Co., Ltd.).

Spherical Silicone Powders

Spherical silicone powders are exemplified by crosslinked silicone powders (i.e., so-called silicone rubber powders composed of organopolysiloxane having a structure in which repeating chains of diorganosiloxane units are crosslinked) and silicone resin particles (polyorganosilsesquioxane resin particles having a three-dimensional network structure). Specific examples are known by names such as (dimethicone/vinyl dimethicone) crosspolymer and polymethylsilsesquioxane. These powders are commercially available as silicone oil-containing swollen powders, examples of which include those sold under the trade names KMP-598, 590, 591 and KSG-016F (all from Shin-Etsu Chemical Co., Ltd.). One or more of these powders may be used.

In particular, silicone resin-coated silicone rubber powders are employed in sunscreens, makeup, concealers and the like on account of their touch-improving effects such as preventing stickiness, and their wrinkle, pore and other shape-correcting effects. Specific examples of silicone resin-coated silicone rubber powders include those known by such names as the following which are defined in the International Nomenclature of Cosmetic Ingredients: (vinyl dimethicone/methicone silsesquioxane) crosspolymer, (diphenyl dimethicone/vinyl diphenyl dimethicone/silsesquioxane) crosspolymer, polysilicone-22 and polysilcone-1 crosspolymer. These are commercially available under such trade names as KSP-100, 101, 102, 105, 300, 411 and 441 (all from Shin-Etsu Chemical Co., Ltd.). One or more of these powders may be used.

(D) Surfactants

The surfactants are exemplified by nonionic, anionic, cationic and amphoteric surfactants, and are not particularly limited. Use can be made of any surfactant used in conventional cosmetic preparations. One surfactant may be used alone or two or more may be used in suitable combination. Of these surfactants, partially crosslinked polyether-modified silicones, partially crosslinked polyglycerol-modified silicones, linear or branched polyoxyethylene-modified organopolysiloxanes, linear or branched polyoxyethylene-polyoxypropylene-modified organopolysiloxanes, linear or branched polyoxyethylene/alkyl co-modified organopolysiloxanes, linear or branched polyoxyethylene-polyoxypropylene/alkyl co-modified organopolysiloxanes, linear or branched polyglycerol-modified organopolysiloxanes and linear or branched polyglycerol/alkyl co-modified organopolysiloxanes are preferred. In these surfactants, the content of hydrophilic polyoxyethylene groups, polyoxyethylene-polyoxypropylene groups or polyglycerol residues preferably accounts for 10 to 70% of the molecule. Specific examples include KSG-210, 240, 310, 320, 330, 340, 320Z, 350Z, 710, 810, 820, 830, 840, 820Z, 850Z, KF-6011, 6013, 6017, 6043, 6028, 6038, 6048, 6100, 6104, 6105, 6106 and KP-578. When this ingredient is included, the content thereof is preferably from 0.01 to 15% of the cosmetic preparation.

(E) Crosslinked Organopolysiloxanes

The crosslinked organopolysiloxanes are not particularly limited, provided they are ones that are used in conventional cosmetics. One crosslinked organopolysiloxane may be used alone or two or more may be used in suitable combination. These crosslinked organopolysiloxanes differ from the (C) silicone powders and (D) surfactants mentioned above in that they are compounds without polyether or polyglycerol moieties in the molecular structure, and are elastomers which, by swelling with an oil, have structural viscosity. Examples include (dimethicone/vinyl dimethicone) crosspolymer, (dimethicone/phenyl vinyl dimethicone) crosspolymer, (vinyl dimethicone/lauryl dimethicone) crosspolymer and (lauryl polydimethylsiloxyethyl dimethicone/bis-vinyl dimethicone) crosspolymer. These are commercially available as swollen products containing an oil that is liquid at room temperature, examples of which include KSG-15, 1510, 16, 1610, 18A, 19, 41A, 42A, 43, 44, 042Z, 045Z and 048Z from Shin-Etsu Chemical Co., Ltd. When this ingredient is included, the content thereof is preferably from 0.01 to 30% of the cosmetic preparation.

(F) Film-Forming Agents Other than Component (A)

The film-forming agent is not particularly limited, provided it is an ingredient that can be included in conventional cosmetic preparations. Specific examples include latexes of polyvinyl alcohol, polyvinyl pyrrolidone, polyvinyl acetate, polyalkyl acrylate, etc.; cellulose derivatives such as dextrin, alkyl cellulose and nitrocellulose; siliconized polysaccharide compounds such as tri(trimethylsiloxy)silylpropylcarbamic acid pullulan, acrylate-silicone graft copolymers such as (alkyl acrylate/dimethicone) copolymers, silicone resins such as trimethylsiloxysilicic acid, silicone-modified polynorbornene, silicone-based resins such as fluorine-modified silicone resins, fluorocarbon resins, aromatic hydrocarbon resins, polymer emulsion resins, terpene resins, polybutenes, polyisoprenes, alkyd resins, polyvinyl pyrrolidone-modified polymers, rosin-modified resins and polyurethanes.

Of these, silicone-based film-forming agents are especially preferred. Examples of silicone-based film-forming agents that may be used include, but are not limited to, tri(trimethylsiloxy)silylpropylcarbamic acid pullulan (commercially available in a solvent-dissolved form as TSPL-30-D5 and ID from Shin-Etsu Chemical Co., Ltd.), (alkyl acrylate/dimethicone) copolymers (available in a solvent-dissolved form as KP-543, 545, 549, 550 and 545L from Shin-Etsu Chemical Co., Ltd.), trimethylsiloxysilicic acid (available in a solvent-dissolved form as KF-7312J and X-21-5250 from Shin-Etsu Chemical Co., Ltd.), silicone-modified polynorbornene (available in a solvent-dissolved form as NBN-30-ID from Shin-Etsu Chemical Co., Ltd.) and organopolyvinyl alcohol-based polymers. One or more film-forming agent may be used. When this ingredient is included, the content thereof is preferably from 0.1 to 20% of the cosmetic preparation.

(G) Aqueous Ingredients

The aqueous ingredients are not particularly limited, provided they are aqueous ingredients that can be included in conventional cosmetic preparations. Exemplary aqueous ingredients include water and humectants. One aqueous ingredient may be used alone or two or more may be used in suitable combination. When an aqueous ingredient is included, the content thereof is preferably from 0.1 to 90% of the cosmetic preparation.

Water

The water is exemplified by purified water commonly used in cosmetic preparations, and also distilled water from fruits and plants, and seawater, thermal spring water and peat water as defined in the International Nomenclature of Cosmetic Ingredients.

Humectants

Examples of humectants include lower alcohols such as ethanol and isopropanol; sugar alcohols such as sorbitol, maltose and xylitol; polyvalent alcohols such as butylene glycol, dibutylene glycol, propylene glycol, dibutylene glycol, pentylene glycol, decanediol, octanediol, hexanediol, erythritol, glycerin, diglycerin and polyethylene glycol; and also glucose, glyceryl glucoside, betaine, hyaluronic acid, chondroitin sulfate, pyrrolidone carboxylate, polyoxyethylene methyl glucoside and polyoxypropylene methyl glucoside.

(H) Waxes

Waxes that may be used in this invention are not particularly limited, provided they are starting materials that can be included in conventional cosmetic preparations. Specific examples include hydrocarbon waxes such as ceresin, ozokerite, paraffin, synthetic waxes, microcrystalline wax and polyethylene wax; vegetable waxes such as carnauba wax, rice wax, rice bran wax, jojoba wax (including extremely hydrogenated jojoba oil) and candelilla wax; and animal waxes such as spermaceti, beeswax and Snow White Wax. When a wax is included, the content thereof is preferably from 0.1 to 10% of the cosmetic preparation.

(I) Other Additives

Examples of other additives include oil-soluble gelling agents, antiperspirants, ultraviolet absorbers, preservatives and bactericides, fragrances, salts, antioxidants, pH adjustors, chelating agents, algefacients, anti-inflammatory agents and skin beautifying ingredients (whitening agents, cell activators, skin roughness improvers, circulation promoting ingredients, skin astringents, antiseborrheic agents, etc.), vitamins, amino acids, water-soluble polymeric compounds, fibers and inclusion compounds.

Oil-Soluble Gelling Agents

Examples of oil-soluble gelling agents include metal soaps such as aluminum stearate, magnesium stearate and zinc myristate; amino acid derivatives such as N-lauroyl-L-glutamic acid and α,γ-di-n-butylamine; dextrin fatty acid esters such as dextrin palmitate, dextrin stearate and dextrin 2-ethylhexanoate palmitate; sucrose fatty acid esters such as sucrose palmitate and sucrose stearate; fructooligosaccharide fatty acid esters such as fructooligosaccharide stearate and fructooligosaccharide 2-ethylhexanoate; benzilidene derivatives of sorbitol such as monobenzylidene sorbitol and dibenzylidene sorbitol; and organic-modified clay minerals such as disteardimonium hectorite, stearalkonium hectorite and hectorite.

Ultraviolet Absorbers

Examples of ultraviolet absorbers include homomenthyl salicylate, octocrylene, 4-tert-butyl-4'-methoxydibenzoyl methane, 4-(2-β-glucopyranosiloxy)propoxy-2-hydroxybenzophenone, octyl salicylate, hexyl 2-[4-(diethylamino)-2-hydroxybenzoyl]benzoate, dihydroxydimethoxybenzophenone, sodium dihydroxydimethoxybenzophenone disulfonate, dihydroxybenzophenone, dimethicodiethyl benzal malonate, 1-(3,4-dimethoxyphenyl)-4,4-dimethyl-1,3-pentanedione, 2-ethylhexyl dimethoxybenzylidene dioxoimidazolidine propionate, tetrahydroxybenzophenone, terephthalylidene dicamphor sulfonic acid, 2,4,6-tris[4-(2-ethylhexyloxycarbonyl)anilino]-1,3,5-triazine, methyl bis(trimethylsiloxy)silyl isopentyl trimethoxycinnamate, drometrizole trisiloxane, 2-ethylhexyl p-dimethylaminobenzoate, isopropyl p-methoxycinnamate, 2-ethylhexyl p-methoxycinnamate, 2,4-bis-[{4-(2-ethylhexyloxy)-2-hydroxy}-phenyl]-6-(4-methoxyphenyl)-1,3,5-triazine, 2-hydroxy-4-methoxybenzophenone, hydroxymethoxybenzophenone sulfonic acid and its trihydrate, sodium hydroxymethoxybenzophenonesulfonate, phenylbenzimidazolesulfonic acid and 2,2'-methylenebis(6-(2H-benzotriazole-2-yl)-4-(1,1,3,3-tetramethylbutyl)phenol. It is possible to use together a UVA absorber (e.g., hexyl diethylaminohydroxybenzoyl benzoate) and a UVB absorber (e.g., ethylhexyl methoxycinnamate); any of these respective absorbers may be combined.

Preservatives and Bactericides

Examples of preservatives and bactericides include alkyl esters of p-oxybenzoic acid, benzoic acid, sodium benzoate, sorbic acid, potassium sorbate, phenoxyethanol, imidazolidinyl urea, salicylic acid, isopropyl methyl phenol, carbolic acid, p-chloro-m-cresol, hexachlorophene, benzalkonium chloride, chlorhexidine chloride, trichlorocarbanilide, iodopropynyl butylcarbamate, polylysine, photosensitizers, silver and plant extracts.

The above-described cosmetic material may be in the form of an emulsion or a nonaqueous system. When the desire is to impart a fresh feel on use, an emulsified form is selected. The emulsified form may be any of the following: an oil-in-water (O/W) emulsion, water-in-oil (W/O) emulsion, oil-in-water-in-oil (O/W/O) emulsion or water-in-oil-in-water (W/O/W) emulsion. When the desire is to obtain an oily feel or water resistance, a nonaqueous composition can be selected. In either of these cases, a good cosmetic preparation can be obtained. In this invention, "nonaqueous composition" refers to a composition which contains substantially no water. Of these forms, W/O emulsions and nonaqueous compositions are preferable because a better water resistance and oil resistance can be obtained.

The cosmetic preparation of the invention is not particularly limited, so long as it is a cosmetic preparation which contains the essential ingredients. It may be used in a variety of products, including beauty essences, milky lotions, creams, hair care products, foundations, makeup bases, sunscreens, concealers, cheek color, lipsticks, gloss, balms, mascaras, eye shadows, eye liners, body makeup, deodorants and nail cosmetics. Of these, makeup cosmetics such as foundations, makeup bases, sunscreens, concealers, cheek color, lipsticks, gloss, balms, mascaras, eye shadows and eye liners, sunscreen cosmetics, and cosmetic materials that impart a sunscreening effect to makeup cosmetics are especially preferred for imparting oil resistance and water resistance. The form of the cosmetic preparation of the invention may be selected from among various forms, including liquids, creams, solids, pastes, gels, mousses, sprays, clays, powders and sticks.

EXAMPLES

The invention is illustrated more fully below by way of Preparation Examples, Examples and Comparative Examples, although the invention is not limited to the following Production Examples and Examples. In these Examples, unless noted otherwise, references to "%" in the composition signify percent by weight. Examples of organic group-modified organosilicon resins are presented in the Preparation Examples, and Examples of cosmetic preparations are presented in the Examples and Comparative Examples.

Preparation Example 1

Preparation of 60% Decamethylcyclopentasiloxane Solution of Organic Group-Modified Organosilicon Resin A reactor was charged with 1,000 g of a 50% decamethylcyclopentasiloxane solution of a powdered hydrosilyl group-containing organosilicon resin of average compositional formula (E1) (weight-average molecular weight, 4,360; amount of hydrogen gas evolution, 35.0 mL/g), 250 g of the polyoxyalkylene of formula (E2), 1,000 g of 2-propanol and 0.8 g of a 0.5% 2-propanol solution of chloroplatinic acid, and the reaction was effected by heating for 6 hours at 80° C. The solvent was then driven off by heating under reduced pressure. Next, 250 g of ethanol was added, following which 5 g of a 5% aqueous solution of sodium hydroxide was added, thereby hydrolyzing unreacted hydrosilyl groups, after which neutralization was carried out by adding 0.63 g of concentrated hydrochloric acid. Following neutralization, 150 g of 0.01 N (mol/L; the same applies below for concentrated hydrochloric acid) aqueous hydrochloric acid was added, thereby hydrolyzing allyl ether groups on the unreacted polyoxyalkylene, and neutralization was carried out with 2.6 g of 5% aqueous sodium bicarbonate. The reaction product was heated under reduced pressure to drive off the solvent and filtration was carried out, giving a decamethylcyclopentasiloxane solution of the organic group-modified organosilicon resin of average compositional formula (E3). The solution had a cloudy appearance.

The decamethylcyclopentasiloxane solution of this organic group-modified organosilicon resin was heated at 120 to 130° C. under reduced pressure to remove the decamethylcyclopentasiloxane. The product thus obtained was a solid powder that had a HLB of 6.7.

Average compositional formula (E1):

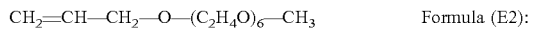

Formula (E2):

Average compositional formula (E3):

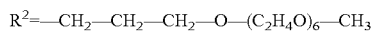

Here and below, "Me" stands for a methyl group.

Preparation Example 2

Preparation of 60% Decamethylcyclopentasiloxane Solution of Organic Group-Modified Organosilicon Resin (Polymer (I))

A reactor was charged with 1,300 g of a 50% decamethylcyclopentasiloxane solution of a powdered hydrosilyl group-containing organosilicon resin of average compositional formula (E4) (weight-average molecular weight, 4,480; amount of hydrogen gas evolution, 8.0 mL/g), 30.7 g of the glycerol monoallyl ether of formula (E5), 1,300 g of 2-propanol and 0.7 g of a 0.5% 2-propanol solution of chloroplatinic acid, and the reaction was effected by heating for 6 hours at 100° C. The solvent was then driven off by heating under reduced pressure. Next, 325 g of ethanol was added, following which 6.5 g of a 5% aqueous solution of sodium hydroxide was added, thereby hydrolyzing unreacted hydrosilyl groups, after which neutralization was carried out by adding 0.8 g of concentrated hydrochloric acid. Following neutralization, 195 g of 0.01 N aqueous hydrochloric acid was added, thereby hydrolyzing allyl ether groups on the unreacted polyoxyalkylene, and neutralization was carried out with 3.3 g of 5% aqueous sodium bicarbonate. The reaction product was heated under reduced pressure to drive off the solvent and filtration was carried out, giving a decamethylcyclopentasiloxane solution of the organic group-modified organosilicon resin of average compositional formula (E6). The solution had an appearance that was clear and colorless.

The decamethylcyclopentasiloxane solution of this organic group-modified organosilicon resin was heated at 120 to 130° C. under reduced pressure to remove the decamethylcyclopentasiloxane. The product thus obtained was a solid powder that had a HLB of 0.9.

Average compositional formula (E4):

$CH_2=CH-CH_2-O-(CH_2CH(OH)CH_2O)-H$  Formula (E5):

Average compositional formula (E6):

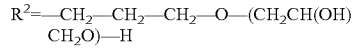

Preparation Example 3

Preparation of 60% Decamethylcyclopentasiloxane Solution of Organic Group-Modified Organosilicon Resin A reactor was charged with 900 g of a 50% decamethylcyclopentasiloxane solution of a powdered hydrosilyl group-containing organosilicon resin of average compositional formula (E10) (weight-average molecular weight, 10,990; amount of hydrogen gas evolution, 37.3 mL/g), 106 g of an organopolysiloxane of formula (E11), 900 g of 2-propanol and 0.7 g of a 0.5% 2-propanol solution of chloroplatinic acid, and the reaction was effected by heating for 6 hours at 95° C. Next, 91.2 g of the polyoxyalkylene of formula (E12) was added and the reaction was continued by 6 hours of heating at 100° C., following which the solvent was driven off by heating under reduced pressure. Next, 225 g of ethanol was added, following which 4.5 g of a 5% aqueous solution of sodium hydroxide was added, thereby hydrolyzing unreacted hydrosilyl groups, after which neutralization was carried out by adding 0.6 g of concentrated hydrochloric acid. Following neutralization, 135 g of 0.01 N aqueous hydrochloric acid was added, thereby hydrolyzing allyl ether groups on the unreacted polyoxyalkylene, and neutralization was carried out with 2.3 g of 5% aqueous sodium bicarbonate. The reaction mixture was then transferred to an autoclave, following which 50 g of Raney nickel was added and reaction was carried out at 100° C. for 3 hours under a stream of hydrogen at a hydrogen pressure of 1 MPa. The reaction product was heated under reduced pressure to drive off the solvent and filtration was carried out, giving a decamethylcyclopentasiloxane solution of the organic group-modified organosilicon resin of average compositional formula (E13). The solution had an appearance that was clear and colorless.

The decamethylcyclopentasiloxane solution of this organic group-modified organosilicon resin was heated at 120 to 130° C. under reduced pressure to remove the decamethylcyclopentasiloxane. The product thus obtained was a solid powder that had a HLB of 2.8.

$(Me_3SiO_{1/2})_{51.9}(HMe_2SiO_{1/2})_{18.3}(Me_2SiO)_{10.2}(SiO_{4/2})_{80.0}$  Average compositional formula (E10):

$CH_2=CH-(SiO(CH_3)_2)_5-Si(CH_3)_3$  Formula (E11):

$CH_2=CH-CH_2-O-(C_2H_4O)_3-H$  Formula (E12):

$(Me_3SiO_{1/2})_{51.9}(R^2Me_2SiO_{1/2})_{12.8}(R^3Me_2SiO_{1/2})_{5.5}(SiO_{4/2})_{80.0}$  Average compositional formula (E13):

$R^2=-CH_2-CH_2-CH_2-O-(C_2H_4O)_3-CH_3$ $R^3=-CH_2-CH_2-(SiO(CH_3)_2)_5-Si(CH_3)_3$

Preparation Example 4

Preparation of 60% Decamethylcyclopentasiloxane Solution of Organic Group-Modified Organosilicon Resin A reactor was charged with 1,100 g of a 50% decamethylcyclopentasiloxane solution of a solid hydrosilyl group-containing organosilicon resin of average compositional formula (E14) (weight-average molecular weight, 4,100; amount of hydrogen gas evolution, 9.3 mL/g), 89.5 g of the polyoxyalkylene of formula (E15), 1,100 g of 2-propanol and 1.2 g of a 0.5% 2-propanol solution of chloroplatinic acid, and the reaction was effected by heating for 6 hours at 85° C. The solvent was then driven off by heating under reduced pressure. Next, 275 g of ethanol was added, following which 5.5 g of a 5% aqueous solution of sodium hydroxide was added, thereby hydrolyzing unreacted hydrosilyl groups, after which neutralization was carried out by adding 0.7 g of concentrated hydrochloric acid. Following neutralization, 165 g of 0.01 N aqueous hydrochloric acid was added, thereby hydrolyzing allyl ether groups on the unreacted polyoxyalkylene, and neutralization was carried out with 2.8 g of 5% aqueous sodium bicarbonate. The reaction product was heated under reduced pressure to drive off the solvent and filtration was carried out. The reaction product was then diluted with decamethylcyclopentasiloxane to an organic group-modified organosilicon resin weight ratio of 60%, thereby giving a 60% decamethylcyclopentasiloxane solution of the organic group-modified organosilicon resin of average compositional formula (E16). The solution had a cloudy appearance.

The decamethylcyclopentasiloxane solution of this organic group-modified organosilicon resin was heated at 120 to 130° C. under reduced pressure to remove the decamethylcyclopentasiloxane. The product thus obtained was a solid powder that had a HLB of 2.8.

$(Me_3SiO_{1/2})_{25.1}(HMe_2SiO_{1/2})_{1.7}(SiO_{4/2})_{32.5}$  Average compositional formula (E14):

$CH_2=CH-CH_2-O-(C_2H_4O)_5(C_3H_6O)_2-CH_3$ $(Me_3SiO_{1/2})_{25.1}(R^2Me_2SiO_{1/2})_{1.7}(SiO_{4/2})_{32.5}$  Average compositional formula (E16):

$R^2=-CH_2-CH_2-CH_2-O-(C_2H_4O)_5(C_3H_6O)_2-CH_3$

Preparation Example 5

Preparation of 60% Decamethylcyclopentasiloxane Solution of Organic Group-Modified Organosilicon Resin A reactor was charged with 800 g of a 50% decamethylcyclopentasiloxane solution of a powdered hydrosilyl group-containing organosilicon resin of average compositional formula (E17) (weight-average molecular weight, 5,020; amount of hydrogen gas evolution, 13.0 mL/g), 41.6 g of the polyoxyalkylene of formula (E18), 800 g of 2-propanol and 0.4 g of a 0.5% 2-propanol solution of chloroplatinic acid, and the reaction was effected by heating for 6 hours at 105° C. The solvent was then driven off by heating under reduced pressure. Next, 200 g of ethanol was added, following which 4.0 g of a 5% aqueous solution of sodium hydroxide was added, thereby hydrolyzing unreacted hydrosilyl groups, after which neutralization was carried out by adding 0.5 g of concentrated hydrochloric acid. Following neutralization, 120 g of 0.01 N aqueous hydrochloric acid was added, thereby hydrolyzing allyl ether groups on the unreacted polyoxyalkylene, and neutralization was carried out with 2.0 g of 5% aqueous sodium bicarbonate. The reaction product was heated under reduced pressure to drive off the solvent and filtration was carried out, thereby giving a decamethylcyclopentasiloxane solution of the organic group-modified organosilicon resin of average compositional formula (E19). The solution had an appearance that was clear and colorless.

The decamethylcyclopentasiloxane solution of this organic group-modified organosilicon resin was heated at 120 to 130° C. under reduced pressure to remove the decamethylcyclopentasiloxane. The product thus obtained was a solid powder that had a HLB of 1.9.

$(Me_3SiO_{1/2})_{29.6}(HMe_2SiO_{1/2})_{2.9}(SiO_{4/2})_{40.4}$  Average compositional formula (E17):

$CH_2=CH-CH_2-O-(C_3H_6O)_3-H$  Formula (E18):

$(Me_3SiO_{1/2})_{29.6}(R^2Me_2SiO_{1/2})_{2.9}(SiO_{4/2})_{40.4}$  Average compositional formula (E19):

$R^2=-CH_2-CH_2-CH_2-O-(C_3H_6O)_3-H$

Preparation Example 6

Preparation of 60% Decamethylcyclopentasiloxane Solution of Organic Group-Modified Organosilicon Resin A reactor was charged with 500 g of a 50% decamethylcyclopentasiloxane solution of a powdered hydrosilyl group-containing organosilicon resin of average compositional formula (E20) (weight-average molecular weight, 7,240; amount of hydrogen gas evolution, 11.8 mL/g), 36.7 g of the polyglycerol of formula (E21), 500 g of ethanol and 0.3 g of a 0.5% 2-propanol solution of chloroplatinic acid, and the reaction was effected by heating for 6 hours at 85° C. The solvent was then driven off by heating under reduced pressure. Next, 125 g of ethanol was added, following which 2.5 g of a 5% aqueous solution of sodium hydroxide was added, thereby hydrolyzing unreacted hydrosilyl groups, after which neutralization was carried out by adding 0.3 g of concentrated hydrochloric acid. Following neutralization, 75 g of 0.01 N aqueous hydrochloric acid was added, thereby hydrolyzing allyl ether groups on the unreacted polyglycerol, and neutralization was carried out with 1.3 g of 5% aqueous sodium bicarbonate. In addition, the reaction mixture was transferred to an autoclave, following which 50 g of Raney nickel was added and reaction was carried out at 100° C. for 3 hours under a stream of hydrogen at a hydrogen pressure of 1 MPa. The reaction product was then heated under reduced pressure to drive off the solvent and filtration was carried out, thereby giving a decamethylcyclopentasiloxane solution of the organic group-modified organosilicon resin of average compositional formula (E22). The solution had a cloudy appearance.

The decamethylcyclopentasiloxane solution of this organic group-modified organosilicon resin was heated at 120 to 130° C. under reduced pressure to remove the decamethylcyclopentasiloxane. The product thus obtained was a solid powder that had a HLB of 2.6.

Average compositional formula (E20):

$CH_2=CH-CH_2-O-(C_2CH(OH)CH_2O)_3-H$    Formula (E21):

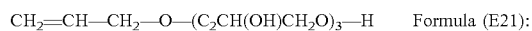

Average compositional formula (E22):

$R^2=-CH_2-CH_2-CH_2-O-(C_2CH(OH)CH_2O)_3-H$

Preparation Example 7

Preparation of 60% Decamethylcyclopentasiloxane Solution of Organic Group-Modified Organosilicon Resin A reactor was charged with 1,300 g of a 50% decamethylcyclopentasiloxane solution of a powdered hydrosilyl group-containing organosilicon resin of average compositional formula (E27) (weight-average molecular weight, 5,210; amount of hydrogen gas evolution, 25.8 mL/g), 325.0 g of the polyoxyalkylene of formula (E28), 1,300 g of ethanol and 1.0 g of a 0.5% 2-propanol solution of chloroplatinic acid, and the reaction was effected by heating for 6 hours at 90° C. The solvent was then driven off by heating under reduced pressure. Next, 325 g of ethanol was added, following which 6.5 g of a 5% aqueous solution of sodium hydroxide was added, thereby hydrolyzing unreacted hydrosilyl groups, after which neutralization was carried out by adding 0.8 g of concentrated hydrochloric acid. Following neutralization, 195 g of 0.01 N aqueous hydrochloric acid was added, thereby hydrolyzing allyl ether groups on the unreacted polyoxyalkylene, and neutralization was carried out with 3.3 g of 5% aqueous sodium bicarbonate. The reaction product was then heated under reduced pressure to drive off the solvent and filtration was carried out, thereby giving a decamethylcyclopentasiloxane solution of the organic group-modified organosilicon resin of average compositional formula (E29). The solution had a cloudy appearance.

The decamethylcyclopentasiloxane solution of this organic group-modified organosilicon resin was heated at 120 to 130° C. under reduced pressure to remove the decamethylcyclopentasiloxane. The product thus obtained was a solid powder that had a HLB of 6.7.

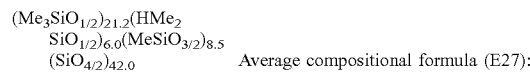

Average compositional formula (E27):

$CH_2=CH-CH_2-O-(C_2H_4O)_2(C_3H_6O)_5-CH_3$    Formula (E28):

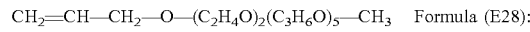

Average compositional formula (E29):

$R^2=-CH_2-CH_2-CH_2-O-(C_2H_4O)_2(C_3H_6O)_5-CH_3$

Preparation Example 8

Preparation of 60% Decamethylcyclopentasiloxane Solution of Organic Group-Modified Organosilicon Resin A reactor was charged with 1,000 g of a 50% decamethylcyclopentasiloxane solution of a powdered hydrosilyl group-containing organosilicon resin of average compositional formula (E30) (weight-average molecular weight, 4,210; amount of hydrogen gas evolution, 6.9 mL/g), 69.1 g of the polyoxyalkylene of formula (E31), 1,000 g of 2-propanol and 0.5 g of a 0.5% 2-propanol solution of chloroplatinic acid, and the reaction was effected by heating for 6 hours at 80° C. The solvent was then driven off by heating under reduced pressure. Next, 250 g of ethanol was added, following which 5.0 g of a 5% aqueous solution of sodium hydroxide was added, thereby hydrolyzing unreacted hydrosilyl groups, after which neutralization was carried out by adding 0.6 g of concentrated hydrochloric acid. Following neutralization, 150 g of 0.01 N aqueous hydrochloric acid was added, thereby hydrolyzing allyl ether groups on the unreacted polyoxyalkylene, and neutralization was carried out with 2.6 g of 5% aqueous sodium bicarbonate. The reaction product was then heated under reduced pressure to drive off the solvent and filtration was carried out, thereby giving a 60% decamethylcyclopentasiloxane solution of the organic group-modified organosilicon resin of average compositional formula (E32). The solution had an appearance that was clear and colorless.

The decamethylcyclopentasiloxane solution of this organic group-modified organosilicon resin was heated at 120 to 130° C. under reduced pressure to remove the decamethylcyclopentasiloxane. The product thus obtained was a solid powder that had a HLB of 1.1.

Average compositional formula (E30):

$CH_2=CH-CH_2-O-(C_2H_4O)_3-CH_3$    Formula (E31):

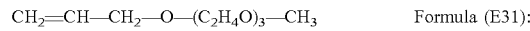

Average compositional formula (E32):

$R^2=-CH_2-CH_2-CH_2-O-(C_2H_4O)_3-CH_3$

The organic group-modified organosilicon resins obtained above were evaluated for their film-forming ability, decamethylcyclopentasiloxane (D5) solubility, and emulsifiability. These results and the physical form of the resin are shown in the following table.

TABLE 1

| Ingredient | Form[1] | Film-forming ability[2] | Film continuity[3] | Film hardness[4] | Appearance when dissolved in D5[5] |
|---|---|---|---|---|---|
| Trimethylsiloxysilicic acid* | solid | yes | no | hard | clear and colorless |

TABLE 1-continued

| Ingredient | Form[1] | Film-forming ability[2] | Film continuity[3] | Film hardness[4] | Appearance when dissolved in D5[5] |
|---|---|---|---|---|---|
| Preparation Example 1 | solid | yes | yes | soft | cloudy |
| Preparation Example 2 | solid | yes | yes | hard** | clear and colorless |
| Preparation Example 3 | solid | yes | yes | soft | clear and colorless |
| Preparation Example 4 | solid | yes | yes | soft | cloudy |
| Preparation Example 5 | solid | yes | yes | soft | clear and colorless |
| Preparation Example 6 | solid | yes | yes | hard** | cloudy |
| Preparation Example 7 | solid | yes | yes | soft | cloudy |
| Preparation Example 8 | solid | yes | yes | hard** | clear and colorless |

[1] Form of 100% ingredient at 25° C.
[2] Does a self-supporting film form when 1.5 g of the solution obtained by dilution with 60% solvent is added dropwise onto a 60 mm diameter aluminum Petri dish and then dried for 3 hours at 105° C.?
[3] Is the film produced in 2) a continuous film (i.e., a film without cracks)?
[4] Can the film produced in 2) be penetrated with a fingernail (when penetrable, it is soft).
[5] Appearance when dissolved in D5; appearance of solution composed of 60% of ingredient and 40% of D5.
*Trimethylsiloxysilicic acid solution; KF-7312J (Shin-Etsu Chemical Co., Ltd.)
**Production Examples 2, 6 and 8 were softer than trimethylsiloxysilicic acid.

Preparation Example 9

Preparation of 60% Isododecane Solution of Polymer (I)

A reactor was charged with 1,300 g of a 50% isododecane solution of a powdered hydrosilyl group-containing organosilicon resin of average compositional formula (E4) (weight-average molecular weight, 4,480; amount of hydrogen gas evolution, 8.0 mL/g), 30.7 g of the glycerol monoallyl ether of formula (E5), 1,300 g of 2-propanol and 0.7 g of a 0.5% 2-propanol solution of chloroplatinic acid, and the reaction was effected by heating for 6 hours at 100° C. The solvent was then driven off by heating under reduced pressure. Next, 325 g of ethanol was added, following which 6.5 g of a 5% aqueous solution of sodium hydroxide was added, thereby hydrolyzing unreacted hydrosilyl groups, after which neutralization was carried out by adding 0.8 g of concentrated hydrochloric acid. Following neutralization, 195 g of 0.01 N aqueous hydrochloric acid was added, thereby hydrolyzing allyl ether groups on the unreacted polyoxyalkylene, and neutralization was carried out with 3.3 g of 5% aqueous sodium bicarbonate. The reaction product was then heated under reduced pressure to drive off the solvent and filtration was carried out, thereby giving an isododecane solution of the organic group-modified organosilicon resin of average compositional formula (E6).

$$(Me_3SiO_{1/2})_{27.8}(HMe_2SiO_{1/2})_{1.6}(SiO_{4/2})_{35.3} \quad \text{Average compositional formula (E4):}$$

$$CH_2=CH-CH_2-O-(CH_2CH(OH)CH_2O)-H \quad \text{Formula (E5):}$$

$$(Me_3SiO_{1/2})_{27.8}(R^2Me_2SiO_{1/2})_{1.6}(SiO_{4/2})_{35.3} \quad \text{Average compositional formula (E6):}$$

$$R^2=-CH_2-CH_2-CH_2-O-(CH_2CH(OH)CH_2O)-H$$

Preparation Example 10

Preparation of 60% Methyl Trimethicone Solution of Polymer (I)

A reactor was charged with 1,300 g of a 50% methyl trimethicone solution of a powdered hydrosilyl group-containing organosilicon resin of average compositional formula (E4) (weight-average molecular weight, 4,480; amount of hydrogen gas evolution, 8.0 mL/g), 30.7 g of the glycerol monoallyl ether of formula (E5), 1,300 g of 2-propanol and 0.7 g of a 0.5% 2-propanol solution of chloroplatinic acid, and the reaction was effected by heating for 6 hours at 100° C. The solvent was then driven off by heating under reduced pressure. Next, 325 g of ethanol was added, following which 6.5 g of a 5% aqueous solution of sodium hydroxide was added, thereby hydrolyzing unreacted hydrosilyl groups, after which neutralization was carried out by adding 0.8 g of concentrated hydrochloric acid. Following neutralization, 195 g of 0.01 N aqueous hydrochloric acid was added, thereby hydrolyzing allyl ether groups on the unreacted polyoxyalkylene, and neutralization was carried out with 3.3 g of 5% aqueous sodium bicarbonate. The reaction product was then heated under reduced pressure to drive off the solvent and filtration was carried out, thereby giving a methyl trimethicone solution of the organic group-modified organosilicon resin of average compositional formula (E6).

$$(Me_3SiO_{1/2})_{27.8}(HMe_2SiO_{1/2})_{1.6}(SiO_{4/2})_{35.3} \quad \text{Average compositional formula (E4):}$$

$$CH_2=CH-CH_2-O-(CH_2CH(OH)CH_2O)-H \quad \text{Formula (E5):}$$

$$(Me_3SiO_{1/2})_{27.8}(R^2Me_2SiO_{1/2})_{1.6}(SiO_{4/2})_{35.3} \quad \text{Average compositional formula (E6):}$$

$$R^2=-CH_2-CH_2-CH_2-O-(CH_2CH(OH)CH_2O)-H$$

Other than D5, isododecane and methyl trimethicone, the resulting polymer can also be dissolved in silicones used in cosmetics, such as dimethicones (e.g., 2 cs and 6 cs), and in ester oils such as triethylhexanoin and isotridecyl isononanoate. The viscosities of these solutions can be changed by way of the polymer composition and molecular weight.

Example 1, Comparative Examples 1 to 5

The W/O foundations shown in Table 3 were produced and subjected to the following evaluations. The Preparation Example ingredient mentioned in the table is the organic group-modified organosilicon resin obtained as described above.

(1) Evaluation of Properties

The cosmetic preparations in the Examples and Comparative Examples were evaluated for the feel on use (lack of stickiness), spreadability, finish (uniformity following application), long-lasting performance (durability: evaluated 8 hours after application), ease of removal (absence of remaining cosmetic after cleansing) and rub-off resistance (absence of secondary adhesion) of the cosmetic according to the criteria shown in Table 1 by ten expert panelists. The evaluation results thus obtained were rated according to the criteria shown below based on the average values for the ten panelists. The results are presented in Tables 3 to 5.

TABLE 2

| Item evaluated | Feel on use | Spreadability | Finish | Durability | Ease of removal | Rub-off resistance |
|---|---|---|---|---|---|---|
| 5 points | good | good | good | good | good | good |
| 4 points | somewhat good | somewhat good | somewhat good | somewhat good | somewhat good | somewhat good |
| 3 points | ordinary | ordinary | ordinary | ordinary | ordinary | ordinary |
| 2 points | somewhat poor | somewhat poor | somewhat poor | somewhat poor | somewhat poor | somewhat poor |
| 1 point | poor | poor | poor | poor | poor | poor |

Rating Criteria

⊚: Average score was 4.5 points or more
○: Average score was at least 3.5 points but less than 4.5 points
Δ: Average score was at least 2.5 points but less than 3.5 points
x: Average score was at least 1.5 points but less than 2.5 points
xx: Average score was less than 1.5 points

TABLE 3

| | Composition (%) | Example 1 | Comparative Example 1 | Comparative Example 2 | Comparative Example 3 | Comparative Example 4 | Comparative Example 5 |
|---|---|---|---|---|---|---|---|
| (1) | Preparation Example 2 (60%) | 3 | | | | | |
| | D5 solution of trimethylsiloxysilicic acid[1] (50%) | | 3.6 | 1.8 | | 1.8 | |
| | D5 solution of highly polymerized dimethylpolysiloxane[2] (20%) | | | | 4.5 | | |
| | D5 solution of acrylic-silicone graft copolymer[3] (30%) | | | | | 3 | 6 |
| | Decamethylcyclopentasiloxane | 3.3 | 6.3 | 2.7 | | 1.5 | 0.3 |
| | Partially crosslinked polyether-modified silicone composition[4] | 3.5 | 3.5 | 3.5 | 3.5 | 3.5 | 3.5 |
| | Partially crosslinked dimethylpolysiloxane composition[5] | 5 | 5 | 5 | 5 | 5 | 5 |
| | Silicone branched polyether-modified silicone[6] | 2 | 2 | 2 | 2 | 2 | 2 |
| | Organic-modified clay mineral | 1.2 | 1.2 | 1.2 | 1.2 | 1.2 | 1.2 |
| | Dimethylpolysiloxane (6 cs) | 6.5 | 6.5 | 6.5 | 6.5 | 6.5 | 6.5 |
| | Decamethylcyclopentasiloxane | 15.3 | 15.3 | 15.3 | 15.3 | 15.3 | 15.3 |
| (2) | Triethylhexanoin | 5 | 5 | 5 | 5 | 5 | 5 |
| | Silicone branched polyglycerol-modified silicone[7] | 0.2 | 0.2 | 0.2 | 0.2 | 0.2 | 0.2 |
| | Silicone-treated titanium oxide[8] | 8.5 | 8.5 | 8.5 | 8.5 | 8.5 | 8.5 |
| | Silicone-treated yellow iron oxide[9] | 0.75 | 0.75 | 0.75 | 0.75 | 0.75 | 0.75 |
| | Silicone-treated red iron oxide[10] | 0.14 | 0.14 | 0.14 | 0.14 | 0.14 | 0.14 |
| | Silicone-treated black iron oxide[11] | 0.01 | 0.01 | 0.01 | 0.01 | 0.01 | 0.01 |
| (3) | Dipropylene glycol | 5 | 5 | 5 | 5 | 5 | 5 |
| | Preservative | QS | QS | QS | QS | QS | QS |
| | Purified water | balance | balance | balance | balance | balance | balance |
| | Total | 100 | 100 | 100 | 100 | 100 | 100 |
| Evaluation of properties | Feel on use | ⊚ | ⊚ | ○ | Δ | ⊚ | ⊚ |
| | Spreadability | ⊚ | ⊚ | ⊚ | X | ⊚ | ○ |
| | Finish | ⊚ | ⊚ | X | Δ | Δ | ⊚ |
| | Durability | ⊚ | XX | X | X | Δ | ○ |
| | Ease of removal | ⊚ | ⊚ | ⊚ | X | X | XX |

[1] Trimethylsiloxysilicic acid solution; KF-7312J (from Shin-Etsu Chemical Co., Ltd.)
[2] Highly polymerized dimethylpolysiloxane solution; KF-9028 (Shin-Etsu Chemical Co., Ltd.
[3] Acrylic-silicone graft copolymer solution; KP-545 (Shin-Etsu Chemical Co., Ltd.)
[4] Partially crosslinked polyether-modified silicone composition; KSG-210 [crosslinked compound: 2 to 30%; dimethylpolysiloxane (6 cs): 70-80%] (Shin-Etsu Chemical Co., Ltd.)
[5] Partially crosslinked dimethylpolysiloxane composition; KSG-15 [crosslinked compound: 4 to 10%; decamethylcyclopentasiloxane: 90 to 96%] (Shin-Etsu Chemical Co., Ltd.)
[6] Silicone branched polyether-modified silicone; KF-6028 (Shin-Etsu Chemical Co., Ltd.)
[7] Silicone branched polyglycerol-modified silicone; KF-6106 (Shin-Etsu Chemical Co., Ltd.)
[8] Silicone-treated titanium oxide; KTP-09W (Shin-Etsu Chemical Co., Ltd.
[9] Silicone-treated yellow iron oxide; KTP-09Y (Shin-Etsu Chemical Co., Ltd.)
[10] Silicone-treated red iron oxide; KTP-09R (Shin-Etsu Chemical Co., Ltd.)
[11] Silicone-treated black iron oxide; KTP-09B (Shin-Etsu Chemical Co., Ltd.)

The ingredient contents are the amounts included in the formulated products shown in the table (the same applies below).

<Preparation of Cosmetic>
A: Component (2) was prepared as a paste on a roll mill.
B: Component (1) was uniformly mixed.
C: Component (3) was uniformly mixed
D: C was added to B and emulsification was carried out, following which A was added, giving a W/O foundation.

It is apparent from the results in Table 3 that the W/O foundation of the invention had a good feel on use (lack of stickiness), spreadability, finish (uniformity following application), long-lasting performance (durability: evaluated 8 hours after application) and ease of removal (absence of remaining cosmetic after cleansing).

Example 2, Comparative Examples 6 to 10

The mascaras shown in Table 4 were produced. The evaluation results too are shown in the table.

TABLE 4

| | Composition (%) | Example 2 | Comparative Example 6 | 7 | 8 | 9 | 10 |
|---|---|---|---|---|---|---|---|
| (1) | Production Example 9 (60%) | 20 | | | | | |
| | Isodododecane solution of trimethylsiloxysilicic acid[1] (60%) | | | 20 | 10 | 10 | |
| | Highly polymerized dimethylpolysiloxane (1,000,000 cs) | | | | 6 | | |
| | Isododecane solution of acrylic-silicone graft copolymer[2] (40%) | | | | | 15 | 30 |
| | Dextrin palmitate[3] | 2 | 2 | 2 | 2 | 2 | 2 |
| | Ceresin | 7 | 7 | 7 | 7 | 7 | 7 |
| | Microcrystalline wax | 7 | 7 | 7 | 7 | 7 | 7 |
| | Isododecane | 30 | 30 | 30 | 30 | 30 | 30 |
| (2) | Organic-modified clay mineral | 5 | 5 | 5 | 5 | 5 | 5 |
| | Silicone-treated black iron oxide[4] | 5 | 5 | 5 | 5 | 5 | 5 |
| | Silicone-treated talc[4] | 5 | 5 | 5 | 5 | 5 | 5 |
| | Polymethylsilsesquioxane[5] | 5 | 5 | 5 | 5 | 5 | 5 |
| | Silicone branched polyether-modified silicone[6] | 1.2 | 1.2 | 1.2 | 1.2 | 1.2 | 1.2 |
| | Propylene carbonate | 1.6 | 1.6 | 1.6 | 1.6 | 1.6 | 1.6 |
| | Preservative | QS | QS | QS | QS | QS | QS |
| | Isododecane | QS | QS | QS | QS | QS | QS |
| Total | | 100 | 100 | 100 | 100 | 100 | 100 |
| Evaluation of properties | Feel on use | ◎ | ◎ | ○ | Δ | ◎ | ◎ |
| | Spreadability | ◎ | ◎ | ◎ | X | Δ | X |
| | Finish | ◎ | ◎ | X | Δ | Δ | ◎ |
| | Durability | ◎ | XX | X | X | Δ | ◎ |
| | Ease of removal | ◎ | ◎ | ◎ | X | X | XX |

[1]Trimethylsiloxysilicic acid solution; X-21-5595 (Shin-Etsu Chemical Co., Ltd.)
[2]Acrylic-silicone graft copolymer solution; KP-550 (Shin-Etsu Chemical Co., Ltd.)
[3]Dextrin palmitate; Rheopearl KL2 (Chiba Flour Milling Co., Ltd.)
[4]Silicone-treated powders obtained by hydrophobizing surface treatment of the respective powders using KF-9909 (Shin-Etsu Chemical Co., Ltd.)
[5]Polymethylsilsesquioxane; KMP-590 (Shin-Etsu Chemical Co., Ltd.)
[6]Silicone branched polyether-modified silicone; KF-6028 (Shin-Etsu Chemical Co., Ltd.)

<Preparation of Cosmetic>
A: Component (1) was uniformly mixed at 85° C.
B: Component (2) was added to A and uniform mixture was carried out at 85° C.
C: B was cooled gradually, giving a mascara.

It is apparent from the results in Table 4 that the mascara of the invention had a good feel on use (lack of stickiness), spreadability, finish (uniformity following application), long-lasting performance (durability: evaluated 8 hours after application) and ease of removal (absence of remaining cosmetic after cleansing).

Example 3, Comparative Examples 11 and 12

The lipsticks shown in Table 5 were produced. The evaluation results too are shown in the table.

TABLE 5

|   | Composition (%) | Example 3 | Comparative Example 11 | Comparative Example 12 |
|---|---|---|---|---|
| (1) | Production Example 2 (60%) | 25 | | |
|   | Decamethylcyclopentasiloxane solution of trimethylsiloxysilicic acid[1] (50%) | | 30 | |
|   | Decamethylcyclopentasiloxane solution of acrylic-silicone graft copolymer[2] (30%) | | | 50 |
|   | Candelilla wax | 9 | 9 | 9 |
|   | Polyethylene | 5 | 5 | 5 |
|   | Silicone wax[3] | 8 | 8 | 8 |
|   | Diisostearyl malate | 4 | 4 | 4 |
|   | Dipentaerythrityl hexahydroxystearate | 1.5 | 1.5 | 1.5 |
|   | Pentaerythrityl tetraisostearate | 6 | 6 | 6 |
|   | Decamethylcyclopentasiloxane | balance | balance | balance |
| (2) | Diglyceryl triisostearate | 4 | 4 | 4 |
|   | Red No. 201 | 0.4 | 0.4 | 0.4 |
|   | Red No. 202 | 0.4 | 0.4 | 0.4 |
|   | Yellow No. 4 | 1.3 | 1.3 | 1.3 |
|   | Silicone-treated black iron oxide[4] | 0.1 | 0.1 | 0.1 |
|   | Silicone-treated titanium oxide[5] | 3.2 | 3.2 | 3.2 |
| (3) | Mica | 6 | 6 | 6 |
|   | Total | 100 | 100 | 100 |
| Evaluation of properties | Feel on use | ○ | Δ | ○ |
|   | Spreadability | ◎ | ◎ | X |
|   | Finish | ◎ | XX | ◎ |
|   | Durability | ◎ | Δ | ◎ |
|   | Ease of removal | ○ | ○ | XX |
|   | Rub-off resistance | ◎ | X | Δ |

[1] Trimethylsiloxysilicic acid solution; KF-7312J (Shin-Etsu Chemical Co., Ltd.)
[2] Acrylic-silicone graft copolymer solution; KP-545 (Shin-Etsu Chemical Co., Ltd.)
[3] Silicone wax; KP-561P (Shin-Etsu Chemical Co., Ltd.)
[4] Silicone-treated black iron oxide; KTP-09B (Shin-Etsu Chemical Co., Ltd.)
[5] Silicone-treated titanium oxide; KTP-09W (Shin-Etsu Chemical Co., Ltd.)

<Preparation of Cosmetic>
A: Component (1) was uniformly mixed at 95° C.
B: Component (2) was formed into a paste on a roll mill.
C: B and component (3) were added to A, following which uniform mixture at 85° C. and then cooling were carried out, giving a lipstick.

It is apparent from the results in Table 5 that the lipstick of the invention had a good feel on use (lack of stickiness), spreadability, finish (uniformity following application), long-lasting performance (durability: evaluated 8 hours after application), ease of removal (absence of remaining cosmetic after cleansing) and rub-off resistance (absence of secondary adhesion).

In the following Examples, the Preparation Example ingredients were obtained as described above.

Example 4

W/O Sunscreen Milk
<Preparation of Cosmetic>
A: Ingredients 1 to 10 were uniformly mixed
B: Ingredients 13 to 17 were uniformly mixed
C: B was added to A and emulsification was carried out, following which Ingredients 11 and 12 were added and uniformly mixed, giving a W/O sunscreen milk.

|   | Composition | % |
|---|---|---|
| 1. | Preparation Example 2 (60%) | 3 |
| 2. | Phenyl-modified partially crosslinked dimethylpolysiloxane composition[1] | 3 |
| 3. | Alkyl/silicone branched polyether-modified silicone[2] | 2 |
| 4. | Decamethylcyclopentasiloxane | 20 |
| 5. | Diphenylsiloxyphenyl trimethicone[3] | 5.5 |
| 6. | Triethylhexanoin | 5 |
| 7. | 2-Ethylhexyl p-methoxycinnamate | 7.5 |
| 8. | Octocrylene | 2.5 |
| 9. | Hexyl 2-[4-(diethylamino)-2-hydroxybenzoyl]benzoate | 1 |
| 10. | Silicone composite powder[4] | 0.5 |
| 11. | Microparticulate titanium oxide dispersion[5] | 5 |
| 12. | Microparticulate zinc oxide powder[6] | 10 |
| 13. | 1,3-Butylene glycol | 3 |
| 14. | Ethanol | 6 |

-continued

| Composition | % |
|---|---|
| 15. Sodium citrate | 0.2 |
| 16. Sodium chloride | 0.5 |
| 17. Purified water | balance |
| Total | 100.0 |

[1] Phenyl-modified partially crosslinked dimethylpolysiloxane composition; KSG-18A [crosslinked compound: 10 to 20%; diphenylsiloxyphenyl trimethicone: 80 to 90%] (Shin-Etsu Chemical Co., Ltd.)
[2] Alkyl/silicone branched polyether-modified silicone; KF-6038 (Shin-Etsu Chemical Co., Ltd.)
[3] Diphenylsiloxyphenyl trimethicone; KF-56A (Shin-Etsu Chemical Co., Ltd.)
[4] Silicone composite powder; KSP-105 (Shin-Etsu Chemical Co., Ltd.)
[5] Microparticulate titanium oxide dispersion; SPD-T5 (Shin-Etsu Chemical Co., Ltd.)
[6] Microparticulate zinc oxide dispersion; SPD-Z5 (Shin-Etsu Chemical Co., Ltd.)

The W/O sunscreen milk thus obtained imparted a light feel on use that was not sticky, spread easily and was not chalky, and it also had a good water resistance and was long-lasting.

Example 5

W/O Sunscreen Milk
<Preparation of Cosmetic>
A: Ingredients 1 to 7 were uniformly mixed
B: Ingredients 10 to 13 were uniformly mixed
C: B was added to A and emulsification was carried out, following which Ingredients 8 and 9 were added and uniformly mixed, giving a W/O sunscreen milk.

| Composition | % |
|---|---|
| 1. Preparation Example 4 (60%) | 2 |
| 2. Partially crosslinked polyether-modified silicone composition[1] | 3 |
| 3. Partially crosslinked dimethylpolysiloxane composition[2] | 2 |
| 4. Silicone branched polyether-modified silicone[3] | 1 |
| 5. Dimethylpolysiloxane (6 cs) | 5 |
| 6. Decamethylcyclopentasiloxane | 3 |
| 7. Isotridecyl isononanoate | 4 |
| 8. Microparticulate titanium oxide dispersion[4] | 25 |
| 9. Microparticulate zinc oxide dispersion[5] | 35 |
| 10. Dipropylene glycol | 2 |
| 11. Sodium citrate | 0.2 |
| 12. Sodium chloride | 1 |
| 13. Purified water | balance |
| Total | 100.0 |

[1] Partially crosslinked polyether-modified silicone composition; KSG-210 [crosslinked compound: 2 to 30%; dimethylpolysiloxane (6 cs): 70 to 80%] (Shin-Etsu Chemical Co., Ltd.)
[2] Partially crosslinked dimethylpolysiloxane composition; KSG-15 [crosslinked compound: 4 to 10%; decamethylcyclopentasiloxane: 90 to 96%] (Shin-Etsu Chemical Co., Ltd.)
[3] Silicone branched polyether-modified silicone; KF-6028 (Shin-Etsu Chemical Co., Ltd.)
[4] Microparticulate titanium oxide dispersion; SPD-T5 (Shin-Etsu Chemical Co., Ltd.)
[5] Microparticulate zinc oxide dispersion; SPD-Z5 (Shin-Etsu Chemical Co., Ltd.)

The W/O sunscreen milk thus obtained imparted a light feel on use that was not sticky, spread easily and was not chalky, and it also had a good water resistance and was long-lasting.

Example 6

W/O Cream Foundation
<Preparation of Cosmetic>
A: Ingredients 9 to 14 were dispersed on a roll mill.
B: Ingredients 1 to 8 were uniformly mixed.
C: Ingredients 15 to 19 were uniformly mixed.
D: C was added to B and emulsification was carried out, following which A was added, giving a W/O cream foundation.

| Composition | % |
|---|---|
| 1. Alkyl-modified partially crosslinked polyether-modified silicone composition[1] | 3.5 |
| 2. Alkyl-modified partially crosslinked dimethylpolysiloxane composition[2] | 6 |
| 3. Alkyl branched polyether-modified silicone[3] | 3 |
| 4. Organic-modified clay mineral | 1.2 |
| 5. Decamethylcyclopentasiloxane | 20 |
| 6. 2-Ethylhexyl p-methoxycinnamate | 7.5 |
| 7. Preparation Example 5 (60%) | 2 |
| 8. Polymethylsilsesquioxane[4] | 2 |
| 9. Ethylhexyl palmitate | 7 |
| 10. Acrylic-silicone graft copolymer[5] | 0.2 |
| 11. Silicone-treated titanium oxide[6] | 8.5 |
| 12. Silicone-treated yellow iron oxide[7] | QS |
| 13. Silicone-treated red iron oxide[8] | QS |
| 14. Silicone-treated black iron oxide[9] | QS |
| 15. 1,3-Butylene glycol | 5 |
| 16. Methyl p-hydroxybenzoate | 0.15 |
| 17. Sodium citrate | 0.2 |
| 18. Sodium chloride | 0.5 |
| 19. Purified water | balance |
| Total | 100.0 |

[1] Alkyl-modified partially crosslinked polyether-modified silicone composition; KSG-330 [crosslinked compound: 15 to 25%; triethylhexanoin: 75 to 85%] (Shin-Etsu Chemical Co., Ltd.)
[2] Alkyl-modified partially crosslinked dimethylpolysiloxane composition; KSG-43 [crosslinked compound: 25 to 35%; triethylhexanoin: 65 to 75%] (Shin-Etsu Chemical Co., Ltd.)
[3] Alkyl branched polyether-modified silicone; KF-6048 (Shin-Etsu Chemical Co., Ltd.)
[4] Polymethylsilsesquioxane; KMP-591 (Shin-Etsu Chemical Co., Ltd.)
[5] Acrylic-silicon graft copolymer; KP-578 (Shin-Etsu Chemical Co., Ltd.)
[6] Silicone-treated titanium oxide; KTP-09W (Shin-Etsu Chemical Co., Ltd.)
[7] Silicone-treated yellow iron oxide; KTP-09Y (Shin-Etsu Chemical Co., Ltd.)
[8] Silicone-treated red iron oxide; KTP-09R (Shin-Etsu Chemical Co., Ltd.)
[9] Silicone-treated black iron oxide; KTP-09B (Shin-Etsu Chemical Co., Ltd.)

The W/O cream foundation thus obtained was not sticky, spread easily, was long-lasting and exhibited no secondary adhesion.

Example 7

W/O Liquid Foundation
<Preparation of Cosmetic>
A: Ingredients 7 to 13 were dispersed on a roll mill.
B: Ingredients 1 to 6 were uniformly mixed.
C: Ingredients 14 to 19 were uniformly mixed.
D: C was added to B and emulsification was carried out, after which A was added, giving a W/O liquid foundation.

| Composition | % |
|---|---|
| 1. Partially crosslinked polyether-modified silicone composition[1] | 3.5 |
| 2. Alkyl branched polyether-modified silicone[2] | 3 |
| 3. Phenyl-modified partially crosslinked dimethylpolysiloxane composition[3] | 5 |
| 4. Organic-modified clay mineral | 1 |
| 5. Diphenylsiloxyphenyl trimethicone[4] | 9 |
| 6. Decamethylcyclopentasiloxane | 15 |
| 7. Isotridecyl isononanoate | 7.5 |
| 8. Production Example 2 (60%) | 1 |
| 9. Metal soap-treated microparticulate titanium oxide (average primary particle size: 20 nm) | 5 |

-continued

| | Composition | % |
|---|---|---|
| 10. | Silicone-treated titanium oxide[5] | 6.5 |
| 11. | Silicone-treated yellow iron oxide[5] | QS |
| 12. | Silicone-treated red iron oxide[5] | QS |
| 13. | Silicone-treated black iron oxide[5] | QS |
| 14. | Glycerol | 2 |
| 15. | Dipropylene glycol | 3 |
| 16. | Phenoxyethanol | 0.2 |
| 17. | Sodium citrate | 0.2 |
| 18. | Sodium chloride | 0.5 |
| 19. | Purified water | balance |
| | Total | 100.0 |

[1] Partially crosslinked polyether-modified silicone composition; KSG-210 [crosslinked compound: 20 to 30%; dimethylpolysiloxane (6 cs): 70 to 80%] (Shin-Etsu Chemical Co., Ltd.)
[2] Alkyl branched polyether-modified silicone; KF-6048 (Shin-Etsu Chemical Co., Ltd.)
[3] Phenyl-modified partially crosslinked dimethylpolysiloxane composition; KSG-18A [crosslinked compound: 10 to 20%; diphenylsiloxyphenyl trimethicone: 80 to 90%] (Shin-Etsu Chemical Co., Ltd.)
[4] Diphenylsiloxyphenyl trimethicone; KF-56A (Shin-Etsu Chemical Co., Ltd.)
[5] Silicone-treated powders obtained by hydrophobizing surface treatment of the respective powders using KF-9901 (Shin-Etsu Chemical Co., Ltd.)

The W/O liquid foundation thus obtained was not sticky, spread easily, was long-lasting and exhibited no secondary adhesion.

Example 8

W/O Stick Foundation
<Preparation of Cosmetic>
A: Ingredients 10 to 16 were dispersed on a roll mill.
B: Ingredients 1 to 9 were heated to 95° C. and uniformly mixed.
C: A and Ingredients 17 and 18 were uniformly mixed and heated to 85° C.
D: C was added to B and emulsification was carried out, after which the emulsion was filled into a stick container and gradually cooled, giving a W/O stick foundation.

| | Composition | % |
|---|---|---|
| 1. | Partially crosslinked polyglycerol-modified silicone composition[1] | 4 |
| 2. | Alkyl/silicone branched polyether-modified silicone[2] | 1.5 |
| 3. | Inulin stearate[3] | 1.5 |
| 4. | Ceresin | 7.5 |
| 5. | Neopentyl glycol diethylhexanoate | 6 |
| 6. | Triethylhexanoin | 4 |
| 7. | Dimethylpolysiloxane (6 cs) | 11.5 |
| 8. | Polymethylsilsesquioxane[4] | 1.5 |
| 9. | Production Example 2 (60%) | 1 |
| 10. | Silicone-treated titanium oxide[5] | 6.5 |
| 11. | Silicone-treated yellow iron oxide[5] | QS |
| 12. | Silicone-treated red iron oxide[5] | QS |
| 13. | Silicone-treated black iron oxide[5] | QS |
| 14. | Lecithin | 0.2 |
| 15. | Polyoxyethylene sorbitan monooleate (20 E.O.) | 0.3 |
| 16. | Dipropylene glycol | 5 |
| 17. | Methyl p-hydroxybenzoate | 0.1 |
| 18. | Purified water | balance |
| | Total | 100.0 |

[1] Partially crosslinked polyglycerol-modified silicone composition; KSG-710 [crosslinked compound: 20 to 30%; dimethylpolysiloxane (6 cs): 70 to 80%] (Shin-Etsu Chemical Co., Ltd.)
[2] Alkyl/silicone branched polyether-modified silicone; KF-6038 (Shin-Etsu Chemical Co., Ltd.)
[3] Inulin stearate; Rheopearl ISK2 (Chiba Flour Milling Co., Ltd.)
[4] Polymethylsilsesquioxane; KMP-590 (Shin-Etsu Chemical Co., Ltd.)
[5] Silicone-treated powders obtained by hydrophobizing surface treatment of the respective powders using KF-9901 (Shin-Etsu Chemical Co., Ltd.)

The W/O stick foundation thus obtained was not sticky, spread easily, was long-lasting and exhibited no secondary adhesion.

Example 9

Lipstick
<Preparation of Cosmetic>
A: Ingredients 9 to 16 were dispersed on a roll mill.
B: Ingredients 1 to 8 were heated to 95° C. and uniformly mixed.
C: A, B and Ingredients 17 and 18 were uniformly mixed and heated to 85° C.
D: C was filled into a stick container, giving a lipstick.

| | Composition | % |
|---|---|---|
| 1. | Synthetic wax | 7 |
| 2. | Microcrystaltine wax | 3 |
| 3. | Silicone wax[1] | 10.5 |
| 4. | Triethylhexanoin | 15.5 |
| 5. | Neopentylglycol diethylhexanoate | 14 |
| 6. | Neopentyl glycol dicaprate | 7 |
| 7. | Hydrogenated polyisobutene | QS |
| 8. | Diphenyl dimethicone[2] | 7.5 |
| 9. | Talc | 0.7 |
| 10. | Red No. 201 | QS |
| 11. | Red No. 202 | QS |
| 12. | Yellow No. 4 | QS |
| 13. | Silicone-treated titanium oxide[3] | 2.7 |
| 14. | Silicone-treated black iron oxide[3] | QS |
| 15. | Silicone-treated red iron oxide[3] | QS |
| 16. | Diglyceryl triisostearate | 4 |
| 17. | Mica | 6 |
| 18. | Preparation Example 2 (60%) | 1 |
| | Total | 100.0 |

[1] Silicone wax; KP-561P (Shin-Etsu Chemical Co., Ltd.)
[2] Diphenyl dimethicone; KF-54HV (Shin-Etsu Chemical Co., Ltd.)
[3] Silicone-treated powders obtained by hydrophobizing surface treatment of the respective powders using KP-574 (Shin-Etsu Chemical Co., Ltd.)

The lipstick thus obtained was not sticky or oily, was free of bleeding and secondary adhesion, and was also confirmed to be long-lasting.

Example 10

Eye Cream
<Preparation of Cosmetic>
A: Ingredients 1 to 7 were uniformly mixed.
B: Ingredients 8 to 12 were uniformly mixed.
C: B was added to A and emulsification was carried out, giving an eye cream.

| | Composition | % |
|---|---|---|
| 1. | Silicone/alkyl-modified partially crosslinked polyether-modified silicone composition[1] | 4 |
| 2. | Silicone/alkyl-modified partially crosslinked dimethylpolysiloxane composition[2] | 6 |
| 3. | Silicone/alkyl branched polyether-modified silicone[3] | 0.5 |
| 4. | Squalane | 12 |
| 5. | Jojova oil | 4.5 |
| 6. | Preparation Example 2 (60%) | 2.5 |
| 7. | Phenyl-modified silicone composite powder[4] | 2 |

Example 11

Wrinkle Conditioner

<Preparation of Cosmetic>
- A: Ingredients 1 to 7 were uniformly mixed.
- B: Ingredient 8 was added to A and mixed, giving a wrinkle conditioner.

| | Composition | % |
|---|---|---|
| 8. | 1,3-Butylene glycol | 7 |
| 9. | Phenoxyethanol | 0.25 |
| 10. | Sodium citrate | 0.2 |
| 11. | Sodium chloride | 0.5 |
| 12. | Purified water | balance |
| | Total | 100.0 |

[1] Silicone/alkyl-modified partially crosslinked polyether-modified silicone composition; KSG-350Z
[crosslinked compound: 20 to 30%; cyclopentasiloxane: 70 to 80%]
(Shin-Etsu Chemical Co., Ltd.)
[2] Silicone/alkyl-modified partially crosslinked dimethylpolysiloxane composition; KSG-045Z
[crosslinked compound: 15 to 25%; cyclopentasiloxane: 75 to 85%]
(Shin-Etsu Chemical Co., Ltd.)
[3] Silicone/alkyl branched polyether-modified silicone; KF-6038 (Shin-Etsu Chemical Co., Ltd.)
[4] Phenyl-modified silicone composite powder; KSP-300 (Shin-Etsu Chemical Co., Ltd.)

The eye cream thus obtained was smooth without being sticky or oily, spread easily, and was confirmed to impart a long-lasting firming sensation.

Example 11

Wrinkle Conditioner

<Preparation of Cosmetic>
- A: Ingredients 1 to 7 were uniformly mixed.
- B: Ingredient 8 was added to A and mixed, giving a wrinkle conditioner.

| | Composition | % |
|---|---|---|
| 1. | Partially crosslinked polyether-modified silicone composition[1] | 5 |
| 2. | Partially crosslinked dimethylpolysiloxane composition[2] | 55 |
| 3. | Partially crosslinked dimethylpolysiloxane composition[3] | 15 |
| 4. | Decamethylcyclopentasiloxane | balance |
| 5. | Highly polymerized dimethylpolysiloxane/D5 mixed solution[4] | 5 |
| 6. | Preparation Example 8 (60%) | 1 |
| 7. | Silicone-modified polysaccharide compound solution[5] | 1 |
| 8. | Silicone composite powder[6] | 12 |
| | Total | 100.0 |

[1] Partially crosslinked polyether-modified silicone composition; KSG-210
[crosslinked compound: 20 to 30%; dimethylpolysiloxane (6 cs): 70 to 80%]
(Shin-Etsu Chemical Co., Ltd.)
[2] Partially crosslinked dimethylpolysiloxane composition; KSG-15
[crosslinked compound: 4 to 10%; decamethylcyclopentasiloxane: 90 to 96%]
(Shin-Etsu Chemical Co., Ltd.)
[3] Partially crosslinked dimethylpolysiloxane composition; KSG-16
[crosslinked compound: 20 to 30%; dimethylpolysiloxane (6 cs): 70 to 80%]
(Shin-Etsu Chemical Co., Ltd.)
[4] Highly polymerized dimethylpolysiloxane/D5 mixed solution; KF-9028 (Shin-Etsu Chemical Co., Ltd.)
[5] Silicone-modified polysaccharide compound solution; TSPL-30-D5 (Shin-Etsu Chemical Co., Ltd.)
[6] Silicone composite powder; KSP-101 (Shin-Etsu Chemical Co., Ltd.)

The wrinkle concealer thus obtained was smooth without being sticky or oily, spread easily and was confirmed to have a durable sealing effect.

Example 12

W/O Sunscreen Cream

<Preparation of Cosmetic>
- A: Ingredients 1 to 8 were uniformly mixed.
- B: Ingredients 9 to 15 were uniformly mixed.
- C: B was added to A and emulsification was carried out, giving a W/O sunscreen.

| | Composition | % |
|---|---|---|
| 1. | Alkyl-modified, partially crosslinked poly glycerol-modified silicone composition[1] | 3 |
| 2. | Alkyl-modified, partially crosslinked dimethylpolysiloxane composition[2] | 3 |
| 3. | Silicone/alkyl branched poly glycerol-modified silicone[3] | 1.5 |
| 4. | Diphenylsiloxyphenyl trimethicone[4] | 11 |
| 5. | 2-Ethylhexyl p-methoxycinnamate | 6 |
| 6. | Octyl salicylate | 1 |
| 7. | Silicone composite powder[5] | 2 |
| 8. | Preparation Example 2 (60%) | 3 |
| 9. | Xanthan gum | 0.3 |
| 10. | Dipropylene glycol | 5 |
| 11. | Glycerin | 3 |
| 12. | Methyl p-hydroxybenzoate | 0.1 |
| 13. | Sodium citrate | 0.2 |
| 14. | Sodium chloride | 0.5 |
| 15. | Purified water | balance |
| | Total | 100.0 |

[1] Alkyl-modified partially crosslinked polyglycerol-modified silicone composition; KSG-840
[crosslinked compound: 25 to 35%; squalane: 65 to 75%]
(Shin-Etsu Chemical Co., Ltd.)
[2] Alkyl-modified partially crosslinked dimethylpolysiloxane composition; KSG-43
[crosslinked compound: 25 to 35%; triethylhexanoin: 65 to 75%]
(Shin-Etsu Chemical Co., Ltd.)
[3] Silicone/alkyl branched poly glycerol-modified silicone; KF-6105 (Shin-Etsu Chemical Co., Ltd.)
[4] Diphenylsiloxyphenyl trimethicone; KF-56A (Shin-Etsu Chemical Co., Ltd.)
[5] Silicone composite powder; KSP-100 (Shin-Etsu Chemical Co., Ltd.)

The W/O sunscreen cream thus obtained was not sticky, spread easily, imparted a light feel on use that was not oily, and also had a good water resistance and durability.

Example 13

W/O Sunscreen Cream

<Preparation of Cosmetic>
- A: Ingredients 1 to 6 were heated to 70° C. and uniformly mixed.
- B: Ingredients 7 to 14 were heated to 70° C. and uniformly mixed.
- C: B was added to A and emulsification was carried out, followed by gradual cooling, giving a sunscreen.

| | Composition | % |
|---|---|---|
| 1. | Hydroxyethylcellulose | 0.3 |
| 2. | Ethanol | 10 |
| 3. | 1,3-Butylene glycol | 6 |
| 4. | Methyl p-hydroxybenzoate | 0.1 |
| 5. | Sodium acrylate/sodium acryloyldimethyltaurate copolymer composition[1] | 2 |
| 6. | Purified water | balance |
| 7. | Preparation Example 2 (60%) | 1 |
| 8. | Diphenylsiloxyphenyl trimethicone[2] | 3 |
| 9. | Partially crosslinked dimethylpolysiloxane composition[3] | 1 |
| 10. | Cetanol | 2 |
| 11. | 2-Ethylhexyl p-methoxycinnamate | 5 |
| 12. | 2,4-Bis[{4-(2-ethylhexyloxy)-2-hydroxy}phenyl]-6-(4-methoxyphenyl)-1,3,5-triazine | 1 |

-continued

| | Composition | % |
|---|---|---|
| 13. | Polyoxyethylene (60) hydrogenated castor oil | 1 |
| 14. | Polyethyl-modified silicone[4] | 0.5 |
| | Total | 100.0 |

[1] Sodium acrylate/sodium acryloyldimethyltaurate copolymer composition; SIMULGEL EG [crosslinked compound, 35 to 50%], from SEPPIC
[2] Diphenylsiloxyphenyl trimethicone; KF-56A (Shin-Etsu Chemical Co., Ltd.)
[3] Partially crosslinked dimethylpolysiloxane composition; KSG-016F [crosslinked compound: 20 to 30%; dimethylpolysiloxane (6 cs): 70 to 80%] (Shin-Etsu Chemical Co., Ltd.)
[4] Polyether-modified silicone; KF-6011 (Shin-Etsu Chemical Co,. Ltd.)

The W/O sunscreen cream thus obtained was not sticky, spread easily, imparted a light feel on use that was not oily, and also had a good water resistance and durability.

Example 14

Mousse Cheek
<Preparation of Cosmetic>
A: Ingredients 1 to 6 were heated to 80° C. and uniformly mixed.
B: Ingredients 7 to 12 were uniformly mixed in a Henschel mixer.
C: B was added to A and gradually cooled, giving a mousse cheek.

| | Composition | % |
|---|---|---|
| 1. | Partially crosslinked dimethylpolysiloxane composition[1] | 28 |
| 2. | Decamethylcyclopentasiloxane | balance |
| 3. | Neopentyl glycol diisostearate | 9 |
| 4. | Inulin stearate[2] | 10 |
| 5. | Amorphous silicic anhydride[3] | 0.5 |
| 6. | Preparation Example 2 (60%) | 1.5 |
| 7. | Silicone-treated titanium oxide[4] | 0.2 |
| 8. | Red No. 202 | QS |
| 9. | Silicone-treated yellow iron oxide[4] | QS |
| 10. | Silicone-treated black iron oxide[4] | QS |
| 11. | Silicone-treated mica[4] | 5.4 |
| 12. | Silicone-treated cericite[4] | 10 |
| | Total | 100.0 |

[1] Partially crosslinked dimethylpolysiloxane composition; KSG-16 [crosslinked compound: 20 to 30%; dimethylpolysiloxane (6 cs): 70 to 80%] (Shin-Etsu Chemical Co., Ltd.)
[2] Inulin stearate; Rheopearl KL2 (Chiba Flour Milling Co., Ltd.)
[3] Amorphous silicic anhydride; AEROSIL 200 (Nippon Aerosil Co., Ltd.)
[4] Silicone-treated powders obtained by hydrophobizing surface treatment of the respective powders using AES-3083 (Shin-Etsu Chemical Co., Ltd.)

The mousse cheek thus obtained was not sticky or oily, spread easily, had excellent adhesion and also was long-lasting.

Example 15

Gel Eye Color
<Preparation of Cosmetic>
A: Ingredients 1 to 5 were heated to 80° C. and uniformly mixed.
B: Ingredients 6 to 9 were added to A, heated to 90° C. and uniformly mixed.
C: The mixture was poured into a container, giving a gel eye color.

| | Composition | % |
|---|---|---|
| 1. | Partially crosslinked dimethylpolysiloxane composition[1] | 10.5 |
| 2. | Squalane | 17 |
| 3. | Dextrin palmitate[2] | 8.5 |
| 4. | Isotridecyl isononanoate | balance |
| 5. | Preparation Example 2 (60%) | 3 |
| 6. | Amorphous silicic anhydride[3] | 0.1 |
| 7. | Silicone composite powder[4] | 5 |
| 8. | Barium sulfate | 9 |
| 9. | Silicone-treated mica[5] | 32.5 |
| | Total | 100.0 |

[1] Partially crosslinked dimethylpolysiloxane composition; KSG-16 [crosslinked compound: 20 to 30%; dimethylpolysiloxane (6 cs): 70 to 80%] (Shin-Etsu Chemical Co., Ltd.)
[2] Dextrin palmitate; Rheopearl KL2 (Chiba Flour Milling Co., Ltd.
[3] Amorphous silicic anhydride; AEROSIL 972 (Nippon Aerosil Co., Ltd.)
[4] Silicone composite powder; KSP-100 (Shin-Etsu Chemical Co., Ltd.)
[5] Silicone-treated mica obtained by hydrophobizing surface treatment of the respective powders using KP-574 (Shin-Etsu Chemical Co., Ltd.)

The gel eye color thus obtained spread easily, was not oily or chalky, and was long-lasting.

Example 16

Powder Foundation
<Preparation of Cosmetic>
A: Ingredients 1 to 4 were uniformly mixed.
B: Ingredients 5 to 14 were uniformly mixed.
C: A was added to B and uniformly mixed in a Henschel mixer. The resulting powder was passed through a mesh, following which it was pressed into a metal compact using a mold, giving a powder foundation.

| | Composition | % |
|---|---|---|
| 1. | 2-Ethylhexyl p-methoxycinnamate | 4 |
| 2. | Diphenylsiloxyphenyl trimethicone[1] | 4.5 |
| 3. | Triethylhexanoin | 1.5 |
| 4. | Silicone/alkyl branched poly glycerol-modified silicone[2] | 0.6 |
| 5. | Preparation Example 2 (60%) | 1 |
| 6. | Silicone-treated mica[3] | 30 |
| 7. | Barium sulfate | 10 |
| 8. | Alkyl-modified silicone composite powder[4] | 5 |
| 9. | Silicone-composite powder[5] | 4 |
| 10. | Silicone-treated talc[3] | balance |
| 11. | Silicone-treated titanium oxide[3] | 6 |
| 12. | Silicone-treated yellow iron oxide[3] | QS |
| 13. | Silicone-treated red iron oxide[3] | QS |
| 14. | Silicone-treated black iron oxide[3] | QS |
| | Total | 100.0 |

[1] Diphenylsiloxyphenyl trimethicone; KF-56A (Shin-Etsu Chemical Co., Ltd.)
[2] Silicone/alkyl branched polyglycerol-modified silicone; KF-6105 (Shin-Etsu Chemical Co., Ltd.)
[3] Silicone-treated powders obtained by hydrophobizing surface treatment of the respective powders using KF-9909 (Shin-Etsu Chemical Co., Ltd.)
[4] Alkyl-modified silicone composite powder; KSP-441 (Shin-Etsu Chemical Co., Ltd.)
[5] Silicone composite powder; KSP-105 (Shin-Etsu Chemical Co., Ltd.)

The powder foundation thus obtained spread easily, had a good durability and exhibited no secondary adhesion.

Example 17

Leave-On Hair Treatment
<Preparation of Cosmetic>
A: Ingredients 1 to 4 were uniformly mixed.
B: Ingredients 7 to 12 were uniformly mixed.
C: B was added to A and emulsification was carried out, following which Ingredients 5 and 6 were added, giving a Leave-On Hair Treatment.

|    | Composition | % |
|----|-------------|---|
| 1. | Partially crosslinked polyglycerol-modified silicone composition[1] | 3 |
| 2. | Partially crosslinked dimethylpolysiloxane composition[2] | 1 |
| 3. | Branched polyether-modified silicone[3] | 0.2 |
| 4. | Dimethylpolysiloxane (6 cs) | 8 |
| 5. | Fragrance | QS |
| 6. | Preparation Example 10 (60%) | 1 |
| 7. | Dipropylene glycol | 8 |
| 8. | Ethanol | 5 |
| 9. | Methyl p-hydroxybenzoate | 0.1 |
| 10. | Sodium citrate | 0.2 |
| 11. | Sodium chloride | 0.5 |
| 12. | Purified water | balance |
|    | Total | 100.0 |

[1] Partially crosslinked polyether-modified silicone composition; KSG-210
[crosslinked compound: 20 to 30%; dimethylpolysiloxane (6 cs): 70 to 80%]
(Shin-Etsu Chemical Co., Ltd.)
[2] Partially crosslinked dimethylpolysiloxane composition; KSG-19
[crosslinked compound: 10 to 20%; decamethylcyclopentasiloxane: 80 to 90%]
(Shin-Etsu Chemical Co., Ltd.)
[3] Branched polyether-modified silicone; KF-6017 (Shin-Etsu Chemical Co., Ltd.)

The Leave-On Hair Treatment thus obtained spread easily and was confirmed to impart luster and smoothness to the hair.

Example 18

Hair Treatment

<Preparation of Cosmetic>

A: Ingredients 1 to 7 were heated to 70° C. and uniformly mixed.

B: Ingredients 8 and 9 were heated to 70° C. and uniformly mixed.

C: B was added to A and emulsification and then gradual cooling were carried out, after which Ingredients 10 and 11 were added, giving a hair treatment.

|    | Composition | % |
|----|-------------|---|
| 1. | Preparation Example 9 (60%) | 0.5 |
| 2. | Cetanol | 2 |
| 3. | Cetyl octanoate | 3 |
| 4. | Behentrimonium chloride | 1 |
| 5. | Butyl p-hydroxybenzoate | 0.1 |
| 6. | Diphenylsiloxphenyl trimethicone[1] | 1 |
| 7. | Propylene glycol | 5 |
| 8. | Hydroxyethylcellulose | 0.1 |
| 9. | Purified water | balance |
| 10. | Amino-modified silicone emulsion[2] | 4 |
| 11. | Fragrance | QS |
|    | Total | 100.0 |

[1] Diphenylsiloxphenyl trimethicone; KF-56A (Shin-Etsu Chemical Co., Ltd.)
[2] Amino-modified silicone emulsion; X-52-2328 (Shin-Etsu Chemical Co., Ltd.)

The hair treatment thus obtained spread easily and was confirmed to impart luster and smoothness to the hair.

Example 19

Hair Oil

<Preparation of Cosmetic>

A: Ingredients 1 to 7 were uniformly mixed, giving a hair oil.

|    | Composition | % |
|----|-------------|---|
| 1. | Preparation Example 10 (60%) | 3 |
| 2. | Diphenylsiloxyphenyl trimethicone[1] | 7 |
| 3. | Diethylhexyl succinate | 10 |
| 4. | Highly polymerized dimethylpolysiloxane mixed solution[2] | 1.5 |
| 5. | Tocopherol | 0.1 |
| 6. | Fragrance | 0.1 |
| 7. | Hydrogenated polyisobutene | balance |
|    | Total | 100.0 |

[1] Diphenylsiloxyphenyl trimethicone; KF-56A (Shin-Etsu Chemical Co., Ltd.)
[2] Highly polymerized dimethylpolysiloxane mixed solution; KF-9030 (Shin-Etsu Chemical Co., Ltd.)

The hair oil thus obtained spread easily and was confirmed to impart luster and smoothness to the hair.

Example 20

Hair Wax

<Preparation of Cosmetic>

A: Ingredients 10 to 16 were heated to 80° C. and uniformly mixed.

B: Ingredients 1 to 9 were heated to 90° C. and uniformly mixed.

C: B was added to A and emulsification was carried out, followed by cooling to room temperature.

D: Ingredients 17 and 18 were added to C and uniform mixture was carried out, giving a hair wax.

|    | Composition | % |
|----|-------------|---|
| 1. | Preparation Example 10 (60%) | 1 |
| 2. | Methyl trimethicone[1] | 10 |
| 3. | Candelilla wax | 14 |
| 4. | Beeswax | 6 |
| 5. | POE glyceryl isostearate | 2 |
| 6. | Glycerol monostearate | 3 |
| 7. | Polyether-modified silicone[2] | 2 |
| 8. | Stearic acid | 2 |
| 9. | 2-Ethylhexyl p-methoxycinnamate | 0.1 |
| 10. | Propylene glycol | 6 |
| 11. | 1,3-Butylene glycol | 6 |
| 12. | Carboxyvinyl polymer | 0.3 |
| 13. | Methyl p-hydroxybenzoate | 0.2 |
| 14. | Phenoxyethanol | 0.3 |
| 15. | Trisodium edetate | QS |
| 16. | Purified water | balance |
| 17. | Potassium hydroxide (10% solution) | QS |
| 18. | Fragrance | QS |
|    | Total | 100.0 |

[1] Methyl trimethicone; TMF-1.5 (Shin-Etsu Chemical Co., Ltd.)
[2] Polyether-modified silicone; KF-6011 (Shin-Etsu Chemical Co., Ltd.)

The hair oil thus obtained had little stickiness, and was confirmed to have a good holding power and antiperspirant effect.

Example 21

Oil-Based Mascara
<Preparation of Cosmetic>
A: Ingredients 1 to 6 were heated to 95° C. and uniformly mixed.
B: Ingredients 7 to 14 were added to A, heated to 90° C. and uniformly mixed.
C: B was gradually cooled, giving an oil-based mascara.

| | Composition | % |
|---|---|---|
| 1. | Preparation Example 4 (60%) | 12 |
| 2. | Isododecane solution of trimethylsiloxysilicic acid[1] | 10 |
| 3. | Dextrin palmitate[2] | 2 |
| 4. | Paraffin wax | 6 |
| 5. | Microcrystalline wax | 7 |
| 6. | Isododecane | 30 |
| 7. | Organic-modified clay mineral | 5.5 |
| 8. | Silicone-treated black iron oxide[3] | 5 |
| 9. | Silicone-treated talc[3] | 5 |
| 10. | Silicone composite powder[4] | 5 |
| 11. | Polyether-modified silicone[5] | 1.2 |
| 12. | Propylene carbonate | 1.6 |
| 13. | Methyl p-hydroxybenzoate | 0.1 |
| 14. | Isododecane | balance |
| | Total | 100.0 |

[1]Isododecane solution of trimethylsiloxysilicic acid; X-21-5595 (Shin-Etsu Chemical Co., Ltd.)
[2]Dextrin palmitate; Rheopearl TL2 (Chiba Flour Milling Co., Ltd.)
[3]Silicone-treated powders obtained by hydrophobizing surface treatment of the respective powders using KF-9909 (Shin-Etsu Chemical Co., Ltd.)
[4]Silicone composite powder; KSP-105 (Shin-Etsu Chemical Co., Ltd.)
[5]Polyether-modified silicone; KF-6017 (Shin-Etsu Chemical Co, Ltd.)

The oil-based mascara thus obtained was confirmed to have a good finish, durability and staying power. Also, by using both a hard, brittle film such as trimethylsiloxysilicic acid and a film having softness such as a silicone-modified acrylic polymer, it is possible to adjust the respective film formabilities and the feel on use, such as the finish.

Example 22

W/O Oil-Based Mascara
<Preparation of Cosmetic>
A: Ingredients 1 to 8 were heated to 95° C. and uniformly mixed.
B: Ingredients 9 to 14 were added to A, heated to 85° C. and uniformly mixed.
C: Ingredients 15 to 17 were heated to 85° C. and uniformly mixed.
D: C was added to B and emulsification was carried out, followed by gradual cooling, giving a W/O oil-based mascara.

| | Composition | % |
|---|---|---|
| 1. | Preparation Example 5 (60%) | 8 |
| 2. | Isododecane solution of acrylic-silicone graft copolymer[1] | 10 |
| 3. | Dextrin (palmitate/ethylhexanoate)[2] | 3 |
| 4. | Silicone wax[3] | 2 |
| 5. | Ceresin | 2.5 |
| 6. | Beeswax | 4.5 |
| 7. | Diphenylsiloxyphenyl trimethicone[4] | 3 |
| 8. | Isododecane | balance |
| 9. | Organic-modified clay mineral | 4 |
| 10. | Silicone-treated black iron oxide[5] | 5 |
| 11. | Silicone-treated talc[5] | 4.5 |
| 12. | Amorphous silicic anhydride[6] | 2.7 |
| 13. | Silicone/alkyl branched polyether-modified silicone[7] | 1 |
| 14. | Propylene glycol | 1.3 |
| 15. | Phenoxyethanol | 0.2 |
| 16. | 1,3-Butylene glycol | 1 |
| 17. | Purified water | 12.8 |
| | Total | 100.0 |

[1]Isododecane solution of acrylic-silicone graft copolymer; KP-550 (Shin-Etsu Chemical Co., Ltd.)
[2]Dextrin (palmitate/ethylhexanoate); Rheopearl TT2 (Chiba Flour Milling Co., Ltd.)
[3]Silicone wax; KP-562P (Shin-Etsu Chemical Co., Ltd.)
[4]Diphenylsiloxyphenyl trimethicone; KF-56A (Shin-Etsu Chemical Co., Ltd.)
[5]Silicone-treated powders obtained by hydrophobizing surface treatment of the respective powders using KF-9909 (Shin-Etsu Chemical Co., Ltd.)
[6]Amorphous silicic anhydride; AEROSIL 972 (Nippon Aerosil Co., Ltd.)
[7]Silicone/alkyl branched polyether-modified silicone; KF-6038 (Shin-Etsu Chemical Co., Ltd.)

The W/O oil-based mascara thus obtained was confirmed to have a good finish, durability and staying power. Also, by using both a hard, brittle film such as trimethylsiloxysilicic acid and a film having softness such as a silicone-modified acrylic polymer, it is possible to adjust the respective film formabilities and the feel on use, such as the finish.

Example 23

Roll-On Antiperspirant
<Preparation of Cosmetic>
A: Ingredients 1 to 4 were uniformly mixed.
B: Ingredients 5 to 12 were uniformly mixed.
C: B was added to A and emulsification was carried out, giving a roll-on antiperspirant.

| | Composition | % |
|---|---|---|
| 1. | Partially crosslinked polyether-modified silicone composition1) | 5 |
| 2. | Silicone branched polyether-modified silicone2) | 0.5 |
| 3. | Preparation Example 4 (60%) | 5 |
| 4. | Decamethylcyclopentasiloxane | 9 |
| 5. | 1,3-Butylene glycol | 5 |
| 6. | Chlorhydroxyaluminum | 0.2 |
| 7. | Benzalkonium chloride | 0.2 |
| 8. | Isopropylmethylphenol | 0.05 |
| 9. | Menthol | 0.05 |
| 10. | Ethanol | 55 |
| 11. | Fragrance | QS |
| 12. | Purified water | balance |
| | Total | 100.0 |

1)Partially crosslinked polyether-modified silicone composition; KSG-210 [crosslinked compound: 20 to 30%; dimethylpolysiloxane (6 cs): 70 to 80%] (Shin-Etsu Chemical Co., Ltd.)
2)Silicone branched polyether-modified silicone; KF-6028 (Shin-Etsu Chemical Co., Ltd.)

The roll-on antiperspirant thus obtained spread easily, did not whiten the skin and was confirmed to have a long-lasting antiperspirant effect.

Example 24

Nail Enamel Overcoat
<Preparation of Cosmetic>
A: Ingredients 5 to 9 were mixed together, Ingredient 4 was added, and uniform mixture was carried out.
B: Ingredients 1 to 3 were added to A and mixed together, giving a nail enamel overcoat.

| | Composition | % |
|---|---|---|
| 1. | Preparation Example 8 (60%) | 5 |
| 2. | Nitrocellulose | 17 |
| 3. | Alkyd resin | 4 |
| 4. | Acetyl triethyl citrate | 5 |
| 5. | Butyl acetate | 29 |
| 6. | Ethyl acetate | 25 |
| 7. | Isopropyl alcohol | 3 |
| 8. | n-Butyl alcohol | 1 |
| 9. | Toluene | balance |
| | Total | 100.0 |

The enamel overcoat thus obtained spread easily, increased the gloss of the enamel and was confirmed to be long-lasting.

The invention claimed is:

1. An organic group-modified organosilicon resin having average compositional formula (1) below $$(R^1{}_3SiO_{1/2})_a(R^2{}_3SiO_{1/2})_b(R^3{}_3SiO_{1/2})_c(R^1{}_2SiO_{2/2})_d \\ (R^1SiO_{3/2})_e(SiO_{4/2})_f \quad (1)$$

wherein each $R^1$, independently, is a $C_1$-$C_{30}$ alkyl, $C_6$-$C_{30}$ aryl or $C_7$-$C_{30}$ aralkyl group, wherein each $R^1$ is optionally substituted with a halogen group, an amino group, or a carboxyl group;

each $R^2$, independently, is a polyoxyalkylene group of general formula (2) below, a polyglycerol group of general formula (3) below, or an $R^1$ group:

$$-(CH_2)_2-C_lH_{2l}-O-(C_2H_4O)_g(C_3H_6O)_hR^4 \quad (2)$$

$$-(CH_2)_2-C_lH_{2l}-O-(CH_2CH(OH)CH_2O)_iR^4 \quad (3)$$

wherein $R^4$ is a substituted or unsubstituted monovalent hydrocarbon group or a hydrogen atom, wherein the subscripts l, g, h and i are integers which satisfy the conditions $0 \leq l \leq 15$, $0 \leq g \leq 5$, $0 \leq h \leq 5$, $0 < g+h \leq 5$, and $0 < i \leq 3$, wherein at least one $R^2$ is a polyoxyalkylene group of general formula (2) or a polyglycerol group of general formula (3);

each $R^3$, independently, is an $R^1$ group, a group of general formula (4), a group of general formula (5), a group of general formula (6) or a group of general formula (7) below:

$$-(CH_2)_2-C_mH_{2m}-(SiOR^1{}_2)_j-SiR^1{}_3 \quad (4)$$

$$-(CH_2)_2-C_mH_{2m}-SiR^1{}_{k1}-(OSiR^1{}_3)_{3-k1} \quad (5)$$

$$-(CH_2)_2-C_mH_{2m}-SiR^1{}_{k1}-(OSiR^1{}_{k2} \\ (OSiR^1{}_3)_{3-k2})_{3-k1} \quad (6)$$

$$-(CH_2)_2-C_mH_{2m}-SiR^1{}_{k1}-(OSiR^1{}_{k2}(OSiR^1{}_{k3} \\ (OSiR^1{}_3)_{3-k3})_{3-k2})_{3-k1} \quad (7)$$

wherein each $R^1$, independently, is as defined above,
the subscripts m, j and k1 to k3 are integers which satisfy the conditions $0 \leq m \leq 5$, $0 \leq j \leq 10$, $0 \leq k1 \leq 2$, $0 \leq k2 \leq 2$ and $0 \leq k3 \leq 2$ wherein at least one $R^3$ being a group of general formula (4), general formula (5), general formula (6) or general formula (7); and
the subscripts a, b, c, d, e and f are numbers which satisfy the conditions $0 \leq a \leq 400$, $0 < b \leq 30$, $0 \leq c \leq 30$, $0 \leq d \leq 320$, $0 \leq e \leq 320$, $0 < f \leq 1,000$ and $0.5 \leq (a+b+c)/f \leq 1.5$,
which resin is a solid.

2. The organic group-modified organosilicon resin of claim 1, wherein the subscripts g and h in general formula (2) are integers which satisfy the conditions $0 \leq g \leq 5$, $0 \leq h \leq 5$ and $0 < g+h \leq 5$, and the subscript i in general formula (3) is an integer which satisfies the condition $0 < i \leq 2$.

3. The organic group-modified organosilicon resin of claim 1, wherein the weight-average molecular weight is from 1,000 to 100,000.

4. The organic group-modified organosilicon resin of claim 1 which has a hydrophilic-lipophilic balance, as determined by Griffin's formula, of from 0.1 to 15.

5. A method for preparing the organic group-modified organosilicon resin of claim 1, comprising the step of hydrosilylating a hydrosilyl group-containing organosilicon resin of average compositional formula (8) below $$(R^1{}_3SiO_{1/2})_a(H_nR^1{}_{3-n}SiO_{1/2})_{b+c}(R^1{}_2SiO_{2/2})_d \\ (R^1SiO_{3/2})_e(SiO_{4/2})_f \quad (8)$$

wherein each $R^1$, independently, is a $C_1$-$C_{30}$ alkyl, $C_6$-$C_{30}$ aryl or $C_7$-$C_{30}$ aralkyl group, wherein each $R^1$ is optionally substituted with a halogen group, an amino group, or a carboxyl group;

the subscripts a, b, c, d, e, and f are integers which satisfy the conditions $0 \leq a \leq 400$, $0 < b \leq 30$, $0 \leq c \leq 30$, $0 \leq d \leq 320$, $0 \leq e \leq 320$, $0 < f \leq 1,000$ and $0.5 \leq (a+b+c)/f \leq 1.5$; and n is an integer that satisfies the condition $1 \leq n \leq 3$, with one or more compound that is selected from alkenyl group-terminated compounds of general formulas (9), (10), (11), (12), (13) and (14) below:

$$CH_2=CH-C_lH_{2l}-O-(C_2H_4O)_g(C_3H_6O)_hR^4 \quad (9)$$

$$CH_2=CH-C_lH_{2l}-O-(CH_2CH(OH)CH_2O)_iR^4 \quad (10)$$

$$CH_2=CH-C_mH_{2m}-(SiOR^1{}_2)_j-SiR^1{}_3 \quad (11)$$

$$CH_2=CH-C_mH_{2m}-SiR^1{}_{k1}-(OSiR^1{}_3)_{3-k1} \quad (12)$$

$$CH_2=CH-C_mH_{2m}-SiR^1{}_{k1}-(OSiR^1{}_{k2} \\ (OSiR^1{}_3)_{3-k2})_{3-k1} \quad (13)$$

$$CH_2=CH-C_mH_{2m}-SiR^1{}_{k1}-(OSiR^1{}_{k2}(OSiR^1{}_{k3} \\ (OSiR^1{}_3)_{3-k3})_{3-k2})_{3-k1} \quad (14)$$

wherein $R^1$ is as defined above, $R^4$ is a substituted or unsubstituted monovalent hydrocarbon group or a hydrogen atom, the subscripts l, g, h and i are integers which satisfy the conditions $0 \leq l \leq 15$, $0 \leq g < 8$, $0 \leq h < 8$, $0 < g+h < 8$ and $0 < i$ 5; and the subscripts m, j and k1 to k3 are integers which satisfy the conditions $0 \leq m \leq 5$, $0 \leq j \leq 10$, $0 \leq k1 \leq 2$, $0$ $k2 \leq 2$ and $0 \leq k3 \leq 2$.

6. A cosmetic preparation comprising from 0.1 to 40 wt % of the organic group-modified organosilicon resin of claim 1.

7. The cosmetic preparation of claim 6 which is a makeup cosmetic or a sunscreen cosmetic.

8. The organic group-modified organosilicon resin of claim 7, wherein the makeup cosmetic is selected from the group consisting of a mascara, a lipstick, a W/O cream foundation, a W/O liquid foundation, a W/O stick foundation, an eye cream, a wrinkle conditioner, a mousse for a cheek, a gel eye color, a powder foundation, a leave-on hair treatment, a hair treatment, a hair oil, a hair wax, a roll-on antiperspirant, and a nail enamel overcoat.

9. The organic group-modified organosilicon resin of claim 1, wherein the subscripts a, b, and c are integers which satisfy the conditions $0 \leq a \leq 100$, $0 < b \leq 30$, and $0 \leq c \leq 30$.

10. The organic group-modified organosilicon resin of claim 1, wherein the subscripts a, b, and c are integers which satisfy the conditions $0 \leq a \leq 50$, $0 < b \leq 30$, and $0 \leq c \leq 30$.

11. The organic group-modified organosilicon resin of claim 1, wherein the subscripts a, b, c, and f are integers which satisfy the condition $0.5 \leq (a+b+c)/f \leq 1.2$.

12. The organic group-modified organosilicon resin of claim 1, wherein the subscripts l, i, and g are integers which satisfy the conditions $0 \leq l \leq 2$, $0 < i \leq 3$ and $1 \leq g \leq 5$.

13. The organic group-modified organosilicon resin of claim 1, wherein the subscripts l, i, and g are integers which satisfy the conditions $0 \leq l \leq 2$, $0 < i \leq 2$ and $1 \leq g \leq 5$.

14. The organic group-modified organosilicon resin of claim 1, wherein the subscripts m and j are integers which satisfy the conditions $0 \leq m \leq 2$, and $0 \leq j \leq 10$.

15. The organic group-modified organosilicon resin of claim 1, which is capable of forming a film.

\* \* \* \* \*